US007819813B2

(12) United States Patent
Nagai et al.

(10) Patent No.: US 7,819,813 B2
(45) Date of Patent: Oct. 26, 2010

(54) GRAPH DISPLAY PROCESSING UNIT AND METHOD THEREOF

(75) Inventors: Ryuji Nagai, Osaka (JP); Shinya Nagata, Kobe (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 1167 days.

(21) Appl. No.: 10/531,447

(22) PCT Filed: Oct. 10, 2003

(86) PCT No.: PCT/JP03/13035

§ 371 (c)(1),
(2), (4) Date: Apr. 14, 2005

(87) PCT Pub. No.: WO2004/034902

PCT Pub. Date: Apr. 29, 2004

(65) Prior Publication Data

US 2006/0100536 A1   May 11, 2006

(30) Foreign Application Priority Data

Oct. 15, 2002   (JP) .............................. 2002-301074

(51) Int. Cl.
*A61B 5/02* (2006.01)
(52) U.S. Cl. ...................................................... 600/508
(58) Field of Classification Search ................. 600/508, 600/523
See application file for complete search history.

(56) References Cited

U.S. PATENT DOCUMENTS

| 5,493,515 | A | 2/1996 | Batchelder et al. |
| 6,251,081 | B1 | 6/2001 | Narimatsu |
| 6,892,093 | B2* | 5/2005 | Brodnick ..................... 600/523 |
| 2006/0047210 | A1* | 3/2006 | Moroki et al. ............... 600/509 |

FOREIGN PATENT DOCUMENTS

| JP | 61-41437 | | 2/1986 |
| JP | 61-41437 | A | 2/1986 |
| JP | 61-219833 | A | 9/1986 |
| JP | 62-186346 | | 8/1987 |
| JP | 62-186346 | A | 8/1987 |

(Continued)

OTHER PUBLICATIONS

English Translation of the International Preliminary Examination Report dated May 17, 2004.

(Continued)

*Primary Examiner*—Carl H Layno
*Assistant Examiner*—Brian T Gedeon
(74) *Attorney, Agent, or Firm*—Jason H. Vick; Sheridan Ross, P.C.

(57) ABSTRACT

A graph display processing device and method that facilitates easy viewing of data with periodicity. With each recognition of a cardiac cycle, a CPU of an electrocardiogram display device (100) finds a point between an R-wave and an S-wave in the cardiac cycle and at two-thirds from the lowest point, as a central point of the cardiocyclic waveform. The CPU determines whether or not the central point is displayed in a central region defined as one-third of the center of a display. When the central point is not in the central region, the CPU performs a scroll process on the electrocardiogram.

3 Claims, 19 Drawing Sheets

FOREIGN PATENT DOCUMENTS

| | | |
|---|---|---|
| JP | 5-141992 | 6/1992 |
| JP | 5-141992 | 6/1993 |
| JP | 5-154118 | 6/1993 |
| JP | 5-154118 A | 6/1993 |
| JP | 06-261871 | 9/1994 |
| JP | 06-261871 A | 9/1994 |
| JP | 1997(HEI9)-140682 | 6/1997 |
| JP | 09-257522 A | 10/1997 |
| JP | 2000-107144 | 4/2000 |
| JP | 2000-107144 A | 4/2000 |

OTHER PUBLICATIONS

The International Search Report.

Okajima, Mitsuhara et al., "Reliability of Cardiogram Systems", I.P.C., p. 312, line 27 to p. 313, line 20.

Greenhut, et al., "Computer Analysis of Physiologic Signals in a Cardiovascular Research Laboratory", Bio. Med., 1991, vol. 21, No. 3, pp. 79-86.

Supplementary European Search Report issued for corresponding EP Patent Application No. 03751446.0, dated May 27, 2009.

Okajima, Mitsuhara et al., "Reliability of Cardiogram Systems", I.P.C., p. 312, line 27 to p. 313, line 20. Nov. 10, 1990.

* cited by examiner

GRAPH DISPLAY PROCESSING UNIT AND METHOD THEREOF

CROSS-REFERENCE TO RELATED APPLICATIONS

All the disclosures, including the specification, claims, drawings and abstract, of Japanese Patent Application No. 2002-301074 (filed on Oct. 15, 2002) are incorporated herein by reference.

TECHNICAL FIELD

The present invention relates to a graph display processing device and method, and more particularly, to a device and method that facilitates viewing of data with periodicity.

BACKGROUND ART

In conventional techniques for displaying data in the form of a graph, the display width or graduations for a graph display area are preset such that a graph of the data can be displayed within the graph display area. At this time, when some of the data goes out of the preset display width, the corresponding part of the graph will not be displayed in the graph display area. Another problem is that depending on fluctuations of data contents, the graph can become too small or too large, making it difficult to grasp the characteristics of the graph.

In cases where biological information such as blood pressure or electrocardiogram, process values from a plant, or the like are displayed as a display object of a graph, such graph display needs to be monitored in real time. Therefore, a technique is particularly required that allows appropriate presentation of a graph within a display, irrespective of fluctuations of data contents.

In order to satisfy such requirements, a technique has been proposed that allows a calculator with a graph display function to change (enlarge, contract) its display width (range) to another, using central coordinates in a display screen or coordinates of a pointer on the display screen as a reference (for example, see Patent Document 1). Patent Document 1: JP-A-SHO 62-186346 (FIG. 2)

With the technique as described above, an enlargement or contraction process can be performed on a graph, using the central coordinates or the position of the pointer in the display screen as a reference. This allows the graph to be displayed in an appropriate size and facilitates grasping of the general tendency of data in the display screen.

However, in cases of graph display of biological information or process values, grasping of certain variation patterns of data may be given priority over grasping of the general tendency of the graph in the display screen. For example, in cases of graphs with periodicity based on data representing sinusoidal, voltage or current, waveforms indicating a cyclic signal from a machine, electrocardiographic data, or the like, portions representative of the periodicity may often be more important to identify.

DISCLOSURE OF THE INVENTION

In view of the above demands, the present invention has an object to provide a graph display processing device and method that facilitates easy viewing of data with periodicity.

1) The present invention provides:
a graph display processing device for displaying data with periodicity in an output region, comprising:
cycle determination means for sequentially receiving data with periodicity to determine an object cycle based on the periodicity of the data; and
display control means for determining, based on data for the object cycle, whether or not data included in the cycle is displayed appropriately as a graph in the output region, and when it is determined that the data included in the cycle is not displayed appropriately as a graph in the output region, correcting a display position of a graph of the data in the output region such that the data included in the cycle is displayed appropriately as a graph in the output region.

Because of these characteristics, even in cases where data included in the cycle is not displayed in the output region, the graph display processing device can display a graph of the data included in the cycle in the output region, by correcting the position of the graph.

Thus, the graph display processing device can securely present the graph included in the cycle to users.

2) The present invention also provides:
a graph display control device for displaying data with periodicity in an output region, comprising:
display control means for determining, based on data for an object cycle based on the periodicity of the data, whether or not data included in the cycle is displayed appropriately as a graph in the output region, and when it is determined that the data included in the cycle is not displayed appropriately as a graph in the output region, correcting a display position of a graph of the data in the output region such that the data included in the cycle is displayed appropriately as a graph in the output region.

Because of these characteristics, even in cases where data included in the cycle is not displayed in the output region, the graph display control device can display a graph of the data included in the cycle in the output region, by correcting the position of the graph.

5) In the present invention, the display control means, or the process of correcting a display position of a graph, is characterized by:
for given data recorded in a first recording region for allowing the data to be recorded therein so as to be displayed as a graph in the output region, and a second recording region for allowing the data to be recorded therein so as to be displayed as a graph in the output region, when it is determined that the data included in the cycle is displayed appropriately as a graph in the output region, outputting the data recorded in the first recording region to the output region; and
when it is determined that the data included in the cycle is not displayed appropriately as a graph in the output region, correcting contents recorded in the second recording region such that the data included in the cycle is displayed appropriately as a graph in the output region, and duplicating the contents recorded in the second recording region to the first recording region, and
outputting the contents duplicated to the first recording region to the output region.

Because of these characteristics, in cases where a graph included in the cycle is not displayed in the output region, the graph display processing device can separate a recording region used to correct recorded contents such that the graph included in the cycle is displayed in the output region, from a recording region used to output the recorded contents to the output region. Thus, the graph display method allows the process of correcting recorded contents and the process for outputting the recorded contents to the output region to be performed promptly.

6) In the present invention, the display control means, or the process of correcting a display position of a graph, is characterized by:

when the cycle determination means, or the process of determining an object cycle, fails to determine an object cycle, not correcting a display position of a graph of the data in the output region.

Because of this characteristic, the graph display processing device can correct the position of a graph only in cases where a graph included in the cycle is not displayed in the output region.

7) In the present invention, the cycle determination means, or the process of determining an object cycle, is characterized by:

determining an object cycle based on a characteristic of the data, and the display control means, or the process of correcting a display position of a graph, is characterized by:

when it is determined that the data included in the cycle is not displayed appropriately as a graph in the output region, changing the display position of the graph in the output region in a direction of variation components of the data with periodicity such that the data included in the cycle is displayed appropriately as a graph in the output region.

Because of these characteristics, even in cases where a graph included in the cycle is not displayed in the output region, the graph display processing device can display the graph included in the cycle in the output region, by changing the display position of the graph in the direction of the variation components of the data.

8) In the present invention, the characteristic may include central portion data relating to a central portion in a cycle, and the display control means, or the means for correcting a display position of a graph, is characterized by:

determining, based on the central portion data, whether or not the central portion in the cycle is positioned in a central region in the output region, to determine whether or not data included in the cycle is displayed appropriately as a graph in the output region, and when it is determined that the data included in the cycle is not displayed appropriately as a graph in the output region, changing the display position of the graph in the output region in a direction of variation components of the data with periodicity such that the central portion in the cycle is positioned in the central region.

Because of these characteristics, the graph display processing device can display a graph included in the cycle appropriately in such an arrangement that a central portion of the graph in the cycle is positioned in the central region.

9) In the present invention, the characteristic is calculated based on a local maximum or a local minimum in the object cycle.

Because of this characteristic, the graph display processing device can display a graph included in the cycle while taking into account the characteristic based on a local maximum or a local minimum of the graph included in the cycle.

10) In the present invention, the data includes electrocardiogram measurement data, and the characteristic is calculated based on any of a P-wave height (P potential), a Q-wave height (Q potential), an R-wave height (R potential), an S-wave height (S potential), or a T-wave height (T potential) of an electrocardiographic waveform.

Because of these characteristics, the graph display processing device can display an electrocardiogram included in the cycle while taking into account the characteristic based on any of a P-wave height (P potential), a Q-wave height (Q potential), an R-wave height (R potential), an S-wave height (S potential), or a T-wave height (T potential) of the electrocardiographic waveform.

11) In the present invention, the data relating to the central portion in the cycle includes data relating to a position dividing a segment between the R-wave height and the S-wave height at a ratio of 1:2.

Because of this characteristic, the graph display processing device can display a graph included in the cycle of the electrocardiographic waveform in a well-balanced arrangement, based on data relating to a position dividing a segment between the R-wave height and the S-wave height at a ratio of 1:2.

12) In the present invention, the cycle determination means, or the process of determining an object cycle, is further characterized by:

determining an object cycle based on a characteristic of the data, and the display control means, or the process of correcting a display position of a graph, is characterized by:

when it is determined that the data included in the cycle is not displayed appropriately as a graph in the output region, changing a display magnification in a direction of the variation components in the output region such that the data included in the cycle is displayed appropriately as a graph in the output region.

Because of these characteristics, even in cases where a graph included in the cycle is not displayed in the output region, the graph display processing device can display the cycle in the output region, by changing the display magnification in the direction of the variation components in the output region.

13) In the present invention, data for the object cycle includes amplitude data relating to an amplitude in a cycle, and the display control means, or the process of correcting a display position of a graph, is characterized by:

determining, based on the amplitude data, whether or not a magnitude of the amplitude in the cycle fits a predetermined amplitude criterion, and when it is determined that the magnitude of the amplitude does not fit the amplitude criterion, changing a display magnification in the direction of the variation components in the output region.

Because of these characteristics, the graph display processing device can display a graph with a magnitude of amplitude not fitting the amplitude criterion in an appropriate size by changing its display magnification by the display control means.

14) In the present invention, the characteristic is calculated based on a local maximum or a local minimum in the object cycle.

Because of this characteristic, the graph display processing device can display the graph in an appropriate size while taking into account the amplitude data based on a local maximum or a local minimum of the graph in the cycle.

15) In the present invention, the data includes electrocardiogram measurement data, and the characteristic is calculated based on any of a P-wave height (P potential), a Q-wave height (Q potential), an R-wave height (R potential), an S-wave height (S potential), or a T-wave height (T potential) of an electrocardiographic waveform.

Because of these characteristics, the graph display processing device can display the graph in an appropriate size while taking into account amplitude data based on any of a P-wave height (P potential), a Q-wave height (Q potential), an R-wave height (R potential), an S-wave height (S potential), or a T-wave height (T potential) of the electrocardiographic waveform.

16) In the present invention, the display control means, or the process of correcting a display position of a graph, is characterized by:

determining whether or not the magnitude of the amplitude based on a value relating to an average of the amplitude data in a plurality of the cycles fits the predetermined amplitude criterion.

Because of this characteristic, the graph display processing device can display the graph with an appropriate magnitude of overall amplitude, irrespective of amplitudes in individual cycles, by taking into account the tendency of amplitudes in a plurality of cycles.

17) In the present invention, the display control means, or the process of correcting a display position of a graph, is characterized by:

when the amplitude data exceeds an upper amplitude criterion, changing the display magnification to double, or when the amplitude data falls short of a lower amplitude criterion, changing the display magnification to half.

Because of these characteristics, the graph display processing device can display a graph with a reduced amplitude by changing the display magnification to double, or in other words, making the display graduations double, in cases of too large an amplitude, while it can display a graph with an increased amplitude by changing the display magnification to half, or in other words, making the display graduations half, in cases of too small an amplitude.

19) In the present invention, the graph display processing device further comprises:

a recording region for allowing the data to be recorded therein so as to be displayed as a graph in the output region, in which the recording region allows the data to be recorded therein so as to be dividable at least for each object cycle determined by the cycle determination means.

Because of this characteristic, the graph display processing device can correct the display position of a graph of the data for each object cycle.

20) In the present invention, the display control means, or the process of correcting a display position of a graph, is further characterized by:

based on the determination of the object cycle, presenting in the output region a recognition mark which allows recognition of the object cycle of the graph, in correlation with the cycle.

Because of this characteristic, the graph display processing device can display a graph in such a manner as to facilitate viewing of the position of a graph for each cycle.

23) The present invention also provides:

a graphical representation that represents a graph based on data with periodicity, in which the graphical representation represents a graph based on the data in an output region, and a position of the graph as a display object in the output region is corrected for each cycle of the data such that a central portion of the graph in the cycle is positioned in a central region in the output region.

Because of these characteristics, the graphical representation can display a graph in such a manner that a central portion of the graph in the cycle is positioned in the central region in the output region.

28) The present invention also provides:

a graph display method for displaying data in an output region, comprising the steps of:

sequentially receiving data, determining whether or not data for a predetermined interval is displayed appropriately as a graph in the output region, and when it is determined that the data is not displayed appropriately as a graph in the output region, correcting the output region such that the data is displayed appropriately as a graph in the output region.

Because of these characteristics, even in cases where a graph for a predetermined interval is not displayed in the output region, the graph display processing device can display the graph for the predetermined interval in the output region, by correcting the position of the graph.

29) The present invention also provides:

an electrocardiogram display method for displaying an electrocardiogram in an output region based on electrocardiogram measurement data, comprising the steps of:

receiving electrocardiogram measurement data including noise which affects a display position of an electrocardiogram;

displaying an electrocardiogram in the output region based on the electrocardiogram measurement data;

determining a cardiac cycle of the electrocardiogram as a display object;

determining, based on data on the cardiac cycle, whether or not an electrocardiogram included in the cardiac cycle is displayed in the output region; and when it is determined that the electrocardiogram included in the cardiac cycle is not displayed in the output region due to a presence of the noise, scrolling the electrocardiogram for the cardiac cycle in the output region in a direction of cardiac electric potential variation components such that the electrocardiogram for the cardiac cycle is displayed in the output region.

Because of these characteristics, even in cases where the waveform shape for the cardiac cycle is not displayed in the output region due to the presence of the noise, the electrocardiogram display method allows display of the waveform shape for the cardiac cycle as a display object, through the scroll process.

30) The present invention also provides:

an electrocardiogram display method for displaying an electrocardiogram while performing a display position correction process such that a cardiac cycle of an electrocardiogram based on electrocardiogram measurement data is displayed in an output region, comprising the steps of:

receiving electrocardiogram measurement data;

determining a cardiac cycle of an electrocardiogram based on the electrocardiogram measurement data; and performing a display position correction process such that an electrocardiogram included in the cardiac cycle is displayed in the output region, in correlation, in terms of timing, with the process of determining a cardiac cycle.

Because of these characteristics, the electrocardiogram display method allows the electrocardiographic waveform to be displayed in the output region, in correlation, in terms of timing, with the determination of the cardiac cycle.

The definitions of the terms used in relation to the present invention will be described below.

The term "data with periodicity" involves the general concept including data in which a data portion defined by a predetermined characteristic tends to be repeated as time elapses. For example, this concept corresponds to data in which a portion expressed by a predetermined function is repeated as time elapses (such as data representing a sine wave), electrocardiogram measurement data (data defined by a characteristic such as a P-wave, a Q-wave, an R-wave, an S-wave or a T-wave), data in which a portion defined by a local maximum (or a maximum) or a local minimum (or a minimum) in a predetermined data range is repeated, or the like.

The term "data included in a cycle" involves the concept including data with one, or more than one cycle. For example, this concept corresponds to a portion with one, or more than one cycle in a sine wave, a portion with one, or more than one cycle of heartbeat (cardiac cycle) in an electrocardiogram, or the like.

The term "determining an object cycle" involves the concept including a case where data included in the cycle is determined directly from data with periodicity, a case where data included in the cycle is determined based on a characteristic determined from data with periodicity, or a case where data with periodicity is plotted as a graph to determine data included in the cycle.

The term "data for an object cycle" involves the concept including data contained in an object cycle, or data to which information of being contained in an object cycle is added. In the embodiments, each data constituting electrocardiographic waveform data recognized as one heartbeat corresponds to the term "data for an object cycle."

The term "characteristic of data" involves the general concept including a subject indicating a characteristic of data. In the embodiments, the concept of "characteristic of data" includes data indicating a P-wave height (P potential), data indicating a Q-wave height (Q potential), data indicating an R-wave height (R potential), data indicating an S-wave height (S potential), data indicating a T-wave height (T potential), data indicating a local maximum of a waveform, data indicating a local minimum of a waveform, data indicating a central point, or data indicating an amplitude value.

The term "displayed appropriately as a graph in an output region" involves the concept including a case where entire data included in a cycle is displayed in an output region, a case where most data included in a cycle is displayed in an output region, a case where the characteristic of data included in a cycle is displayed in a recognizable manner in an output region, or a case where data included in a cycle is displayed in an appropriate size in an output region.

The term "not displayed appropriately as a graph in an output region" involves the concept including a case where any data included in a cycle is not displayed in an output region, a case where most data included in a cycle is not displayed in an output region, a case where the characteristic of data included in a cycle is not displayed in a recognizable manner in an output region, or a case where data included in a cycle is not displayed in an appropriate size in an output region. For example, in cases of an electrocardiographic waveform, the concept of "not displayed appropriately as a graph in an output region" includes a state where a waveform is positioned in an upper part of an output region and therefore an upper part of an R-wave is not shown while P-, Q-, S- and T-waves are recognizable.

The term "central portion in a cycle" involves the concept including a portion representing a physical center of data included in a cycle, a portion representing a gravity center of the shape indicated by data included in a cycle, a portion representing a center relating to the time width of data included in a cycle, or a portion representing a virtual center selected to display a characteristic portion of data included in a cycle. The term "portion" as used in central portion involves the concept including an object that can be expressed as a point, or an object that can be expressed as a shape with a certain area. In the embodiments, for example, a point dividing an R-S segment at a ratio of 1:2, shown as a point 44 in FIG. 4, corresponds to the "central portion in a cycle."

The term "variation components of data with periodicity" involves the concept including components in data with periodicity that vary as time elapses. In the embodiments, electric potential values in electrocardiographic waveform data correspond to the "variation components of data with periodicity."

The term "direction of variation components" involves the concept including a direction in which variation components of data vary in a case where data that varies as time elapses is displayed in the form of a graph. In the embodiments, the direction of an axis perpendicular to the time axis (the direction of the electric potential axis) of an electrocardiogram corresponds to the "direction of variation components of data."

The term "changing a display magnification" includes changing a display magnification, changing a display reduction ratio, or changing display graduations. The term "changing" includes increasing or reducing a display magnification or reduction ratio. In the embodiments, the procedures of the scale change process correspond to the "changing a display magnification."

The term "recognition mark which allows recognition of an object cycle" involves the general concept including a mark, a symbol, a figure or a character associated with the position of a cycle. In the embodiments, a recognition point 1105 (see FIG. 11) plotted at the position of an R-wave of each heartbeat corresponds to the "recognition mark."

The features of the present invention have been described broadly as above. The construction and details of the present invention, as well as the features and effects thereof, will become more apparent from the following disclosure when considered in conjunction with the drawings.

BEST MODE FOR CARRYING OUT THE INVENTION

Figure 1:
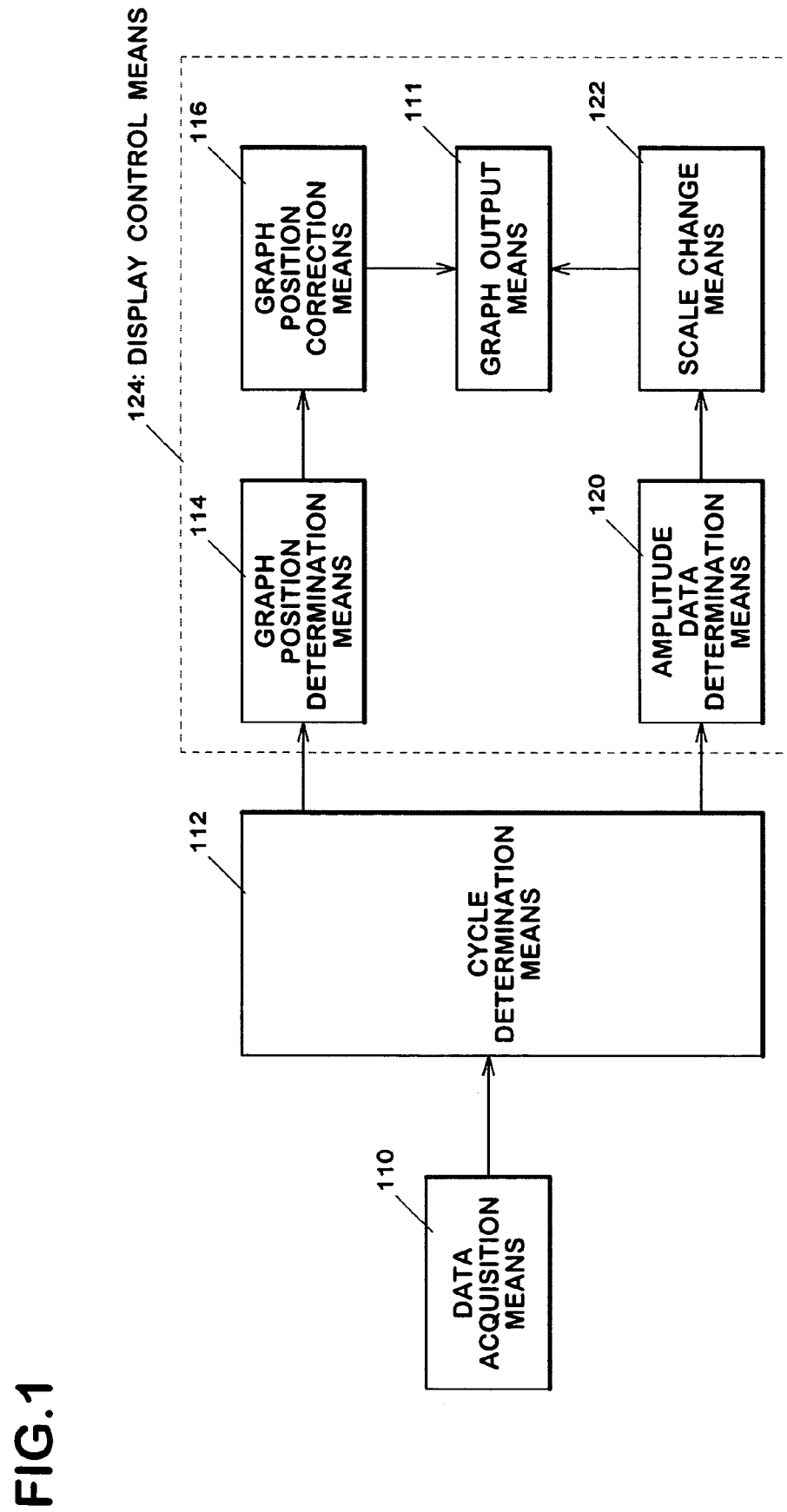
FIG. 1 is a functional block diagram of an electrocardiogram display device.

The present invention can be put into practice as a device which graphically represents data on physical quantities with certain periodicity (which may include biological information). Specifically, the present invention allows monitoring a machine, determining its failure status, and so on, based on the graphical representation of an electric current or voltage waveform as a periodic signal from the machine. The present invention can also adopt data representing optical waveforms, sound waveforms, seismic waveforms, and the like.

In the descriptions below, embodiments of the present invention are presented that utilize data on an "electrocardiogram" as an example of such physical quantities. An electrocardiogram display device as an embodiment of the "graph display processing device" according to the present invention exemplifies a process of presenting an electrocardiogram of a patient on a display. According to an embodiment, when an electrocardiographic waveform of a patient is going to go out of the display, for example due to the presence of noise because of a body movement of the patient, a predetermined scroll process can be performed to display the electrocardiographic waveform within the display (first embodiment). Also, when the amplitude of an electrocardiographic waveform is too large or too small for presentation on a display, a predetermined scale change process can be performed to allow the electrocardiographic waveform to be displayed on a changed scale to facilitate viewing (second embodiment).

Now, the outline of the electrocardiogram display process, the hardware configuration of the device, the correspondence between the terms used in the claims and the embodiments are described, and then the respective embodiments and the like are described.

Contents
1. Outline of Electrocardiogram Display Process
2. Hardware Configuration, etc.
3. Correspondence between Terms Used in Claims and Embodiments
4. Outline of Electrocardiographic Waveform
5. First Embodiment (Scroll Process)
6. Second Embodiment (Scale Change Process)
7. Effects of Embodiments
8. Other Functions of Electrocardiogram Display Device
9. Other Embodiments, etc.

1. Outline of Electrocardiogram Display Process

An electrocardiogram display device 100 for presenting an electrocardiogram on a display is suitable for use in emergency situations, ambulances and hospitals. In the embodiments, descriptions will be made taking as an example a case where the device is used by an emergency medical technician in an ambulance carrying a patient. The configuration of the electrocardiogram display device 100 will be described later.

1-1. Outline of Scroll Process (First Embodiment)

FIG. 6 is a schematic diagram illustrating a scroll process for an electrocardiogram according to the first embodiment to be described later. The vertical axis of the electrocardiogram represents an electric potential value (voltage value) (in millivolt (mV)), and the horizontal axis represents time (in second). The electrocardiogram is drawn (plotted) from left to right in a display area as the measurement time for the electrocardiogram elapses.

Figure 6A:
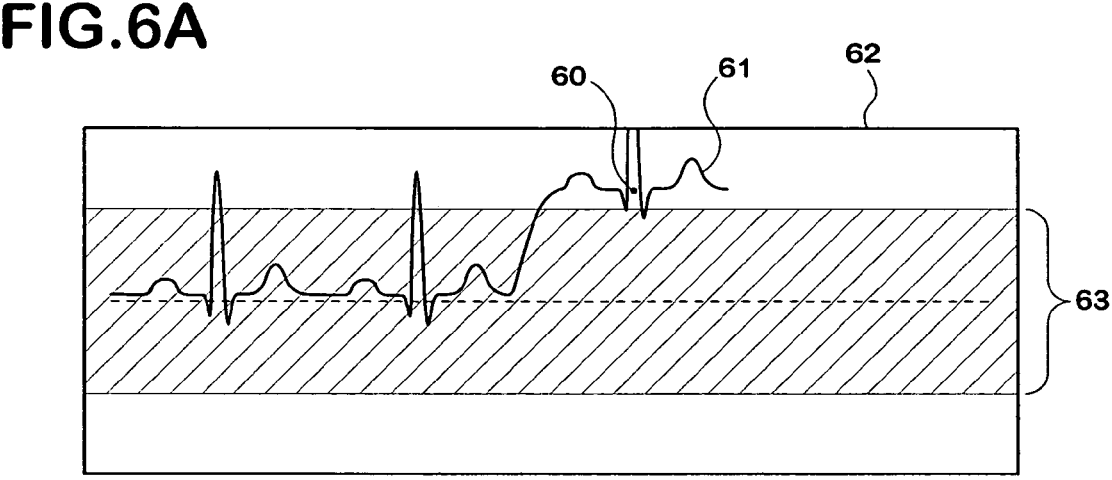
FIG. 6A and FIG. 6B are schematic diagrams illustrating a scroll process according to a first embodiment.

FIG. 6A shows an example of a presentation on the display before the scroll process. An electrocardiogram 61 is displayed in a display area 62. In the scroll process, a predetermined scroll process is performed when the most recent cardiocyclic waveform (a waveform corresponding to one heartbeat) is not so positioned in the display area 62 as to be viewable.

In the embodiment, a state where a cardiocyclic waveform is not so positioned in the display area 62 as to be viewable is defined, for example, as a state where a central point (gravity center point) of a waveform corresponding to a cardiac cycle (one heartbeat) is not within the central one-third of the display area. Specifically, a determination as to whether or not a scroll process is performed is made by a CPU of the electrocardiogram display device 100 as follows. With each recognition of a cardiac cycle, the CPU finds a point between an R-wave and an S-wave in the cardiac cycle (see FIG. 3) and two-thirds the way up from the lowest point, as a central point 60 of the cardiocyclic waveform. The CPU then determines whether or not the central point 60 is displayed in a central region 63 (a central region in an output region) defined as the central one-third of the display area 62. In FIG. 6A, the central point 60 of the most recent cardiocyclic waveform is not within the central region 63 and therefore the CPU of the electrocardiogram display device 100 performs a scroll process on the electrocardiogram 61.

Figure 6B:
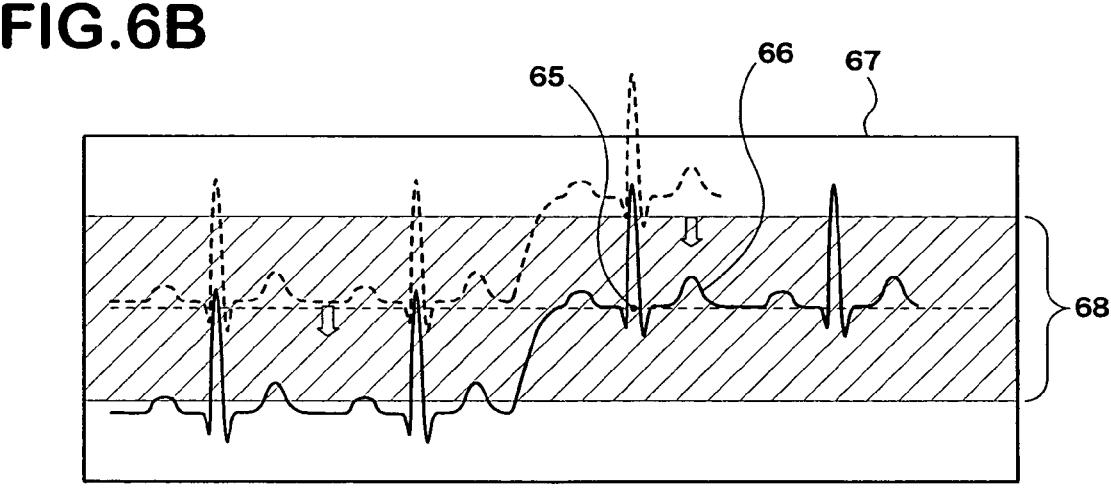

FIG. 6B shows an electrocardiogram after the scroll process. After the scroll process, the electrocardiogram has been translated downward (in a direction of variation components of the data with periodicity) relative to the display area as compared to FIG. 6A, allowing the entire cardiocyclic waveform, which has been difficult to view in FIG. 6A, to be viewed more distinctly. Specifically, the scroll process is performed such that a central point 65 of a cardiocyclic waveform comes to the center of a central region 68 (the central portion of a central region in an output region).

The central regions 63, 68 and an electrocardiogram shown by a dotted line in FIG. 6B are shown for illustration purposes and not actually displayed. However, they may be displayed in the display area.

As has been described above, in the first embodiment, the device displays an electrocardiogram, recognizes an electrocardiographic waveform for each heartbeat, determines based on the recognition results whether or not a cardiocyclic waveform corresponding to a particular heartbeat is displayed appropriately in the display area, and if it is not, performs a scroll process. In this manner, the electrocardiogram display device 100 can appropriately present on the display the shape of an electrocardiographic waveform (including the shape of a QRS wave, etc.), important in assisting determination of the presence or absence of a heart disease, for a user of the device (doctor, emergency medical technician, etc.).

1-2. Outline of Scale Change Process (Second Embodiment)

FIG. 12 is a schematic diagram illustrating a scale change process for an electrocardiogram according to the second embodiment to be described later. The vertical axis of the electrocardiogram corresponds to a range from −(minus) 1 mV to +(plus) 1 mV before the scale change process.

Figure 12A:
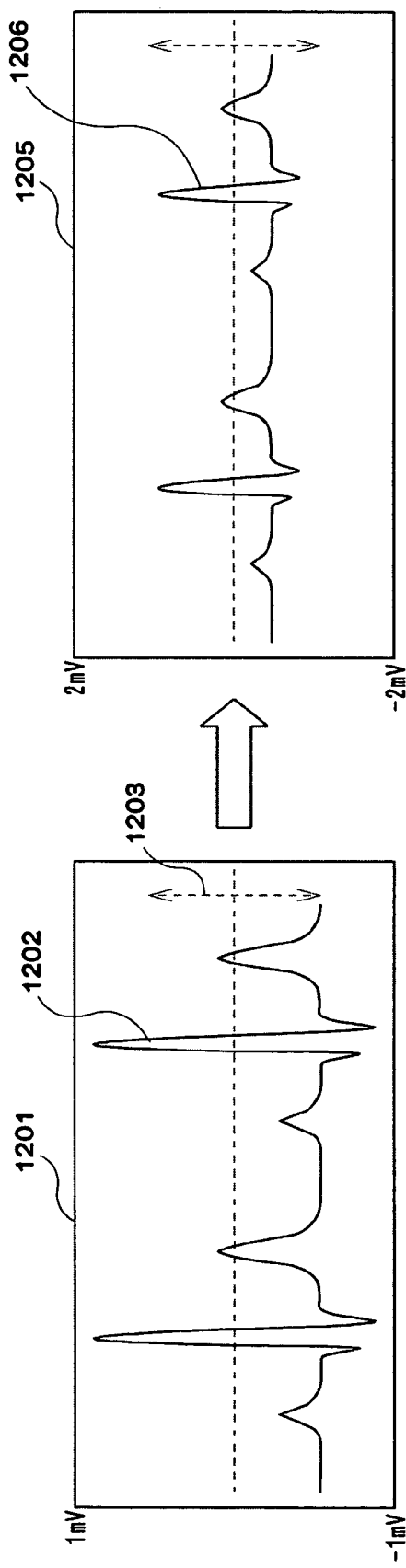
FIG. 12A and FIG. 12B are schematic diagrams illustrating a scale change process according to a second embodiment.

FIG. 12A shows examples of a presentation on the display before and after a process to change the scale to double. An electrocardiogram 1202 is displayed in a display area 1201. In the scale change process, if the amplitude of an electrocardiographic waveform (for example, the electric potential difference between an R-wave height and an S-wave height) for a predetermined heartbeat is larger than the electric potential difference corresponding to half the vertical dimension of the display area (a reference line 1203), the display scale for the display area is made double (the scale for an output region is changed).

Specifically, a CPU of the electrocardiogram display device 100 sets the scale for a display area 1205 to a range from −(minus) 2 mV to +(plus) 2 mV through a scroll change process, thereby resulting in a presentation of an electrocardiogram 1206 compressed such that the amplitude is reduced.

Figure 12B:
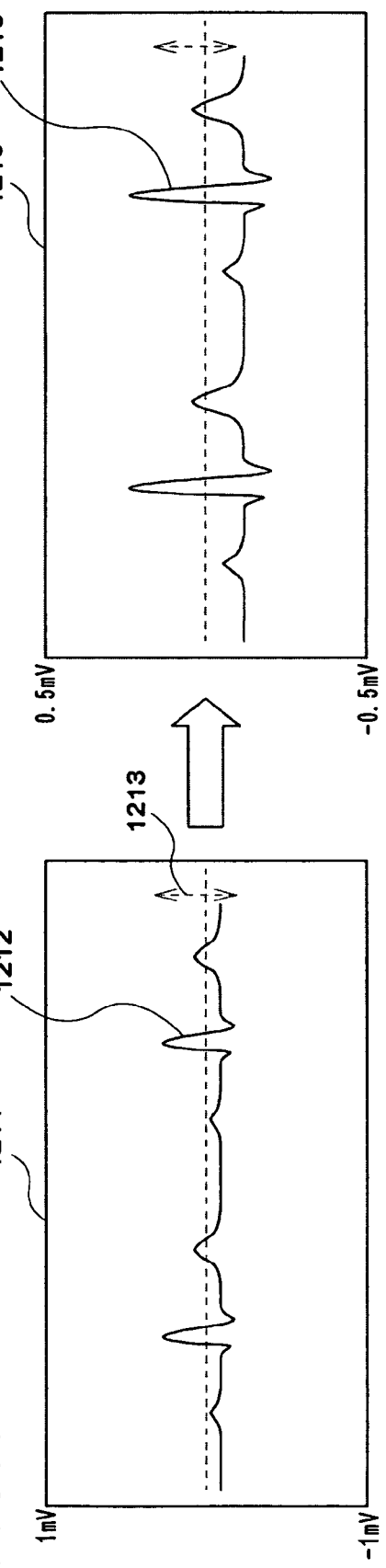

FIG. 12B shows examples of a presentation on the display before and after a process to change the scale to half. An electrocardiogram 1212 is displayed in a display area 1211. In the scale change process, if the amplitude of an electrocardiographic waveform (for example, the electric potential difference between an R-wave height and an S-wave height) for a predetermined heartbeat is smaller than the electric potential difference corresponding to one-fifth of the vertical dimension of the display area (a reference line 1213), the display scale for the display area is made half (the scale for an output region is changed). Specifically, the CPU of the electrocardiogram display device 100 sets the scale for a display area 1215 to a range from −(minus) 0.5 mV to +(plus) 0.5 mV through a scroll change process, thereby resulting in a presentation of an electrocardiogram 1216 expanded such that the amplitude is increased.

The reference lines 1203, 1213 are shown for illustration purposes and not actually displayed. However, they may be displayed in the display area.

As has been described above, in the second embodiment, the device displays an electrocardiogram, and performs a scale change process so as to display a compressed electrocardiogram if the amplitude is too large, or an expanded electrocardiogram if the amplitude is too small. In this manner, the electrocardiogram display device 100 can present on the display the shape of an electrocardiographic waveform (including the shape of a QRS wave) of an appropriate size, important in assisting determination of the presence or absence of a heart disease, for a user of the device.

2. Hardware Configuration

FIG. 1 is a functional block diagram of an electrocardiogram display device. The electrocardiogram display device includes data acquisition means 110, cycle determination means 112, and display control means 124. The display control means 124 includes graph output means 111, graph position determination means 114, graph position correction means 116, amplitude data determination means 120, and scale change means (display magnification change means) 122.

The data acquisition means 110 acquires electrocardiogram measurement data. The graph output means 111 (the display control means 124) presents the electrocardiogram measurement data in the form of a graph on a display.

The cycle determination means 112 determines a cardiac cycle (corresponding to one heartbeat) in the electrocardiogram measurement data. The graph position determination means 114 (the display control means 124) determines, based on central portion data relating to the central portion in a particular cycle, whether or not the data included in the cardiac cycle is displayed in the display area. The graph position correction means 116 (the display control means 124) performs a scroll process on the position of the graph such that the data included in the cardiac cycle will be displayed in the display area.

The amplitude data determination means 120 (the display control means 124) determines, based on amplitude data relating to the amplitude in a particular cycle, whether or not the magnitude of amplitude of the data included in the cardiac cycle (corresponding to one heartbeat) fits a predetermined amplitude criterion. The scale change means 122 (the display control means 124) changes the scale for display.

Figure 2:
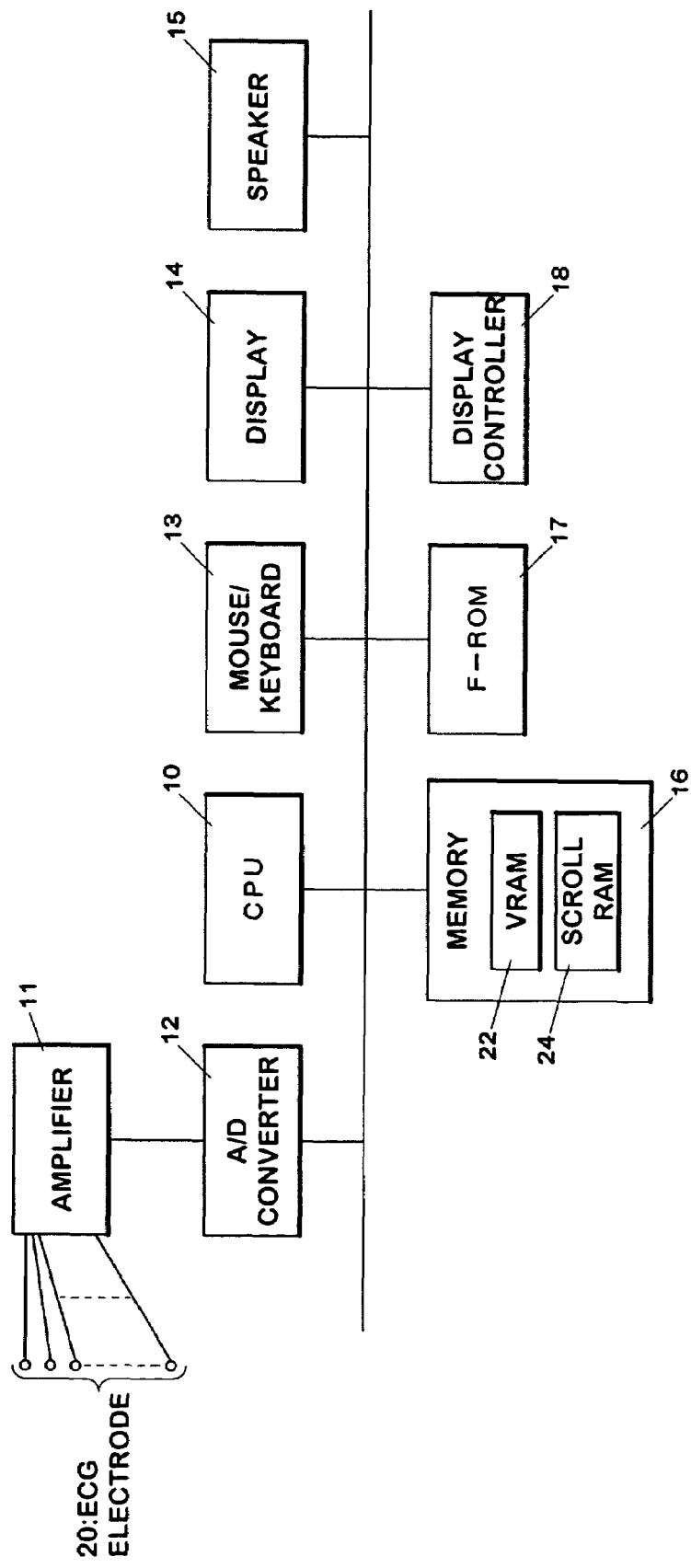
FIG. 2 shows an example of hardware configuration of the electrocardiogram display device.

FIG. 2 shows an example of hardware configuration of the electrocardiogram display device shown in FIG. 1, implemented using a CPU. The electrocardiogram display device 100 includes a CPU 10, an amplifier 11, an A/D converter 12, a mouse/keyboard 13, a display 14 (display device), a speaker 15, a memory 16, a Flash-ROM 17 (a rewritable read-only memory that can store data in an electrically erasable manner, such as flash memory; hereinafter referred to as F-ROM 17), a display controller 18, and ECG electrodes 20 (biological signal detectors).

The ECG electrode 20 is an electrode used to measure a cardiac electric current of a patient. The amplifier 11 amplifies the cardiac electric current obtained by the ECG electrodes 20. The CPU 10 performs a process of converting the obtained cardiac electric current into electrocardiogram measurement data, a graph drawing process, a scroll process, a scale change process and the like, as well as total control of the electrocardiogram display device 100. The F-ROM 17 has recorded therein a program for controlling the electrocardiogram display device 100. The memory 16 provides a workspace for the CPU 10 and the like. Also, the memory 16 includes a Video Random Access Memory 22 (hereinafter referred to as VRAM 22) and a scroll RAM 24 (RAM for scroll). Operation information generated by operating the mouse/keyboard 13 or the display controller 18 is inputted into the CPU 10, and image information and sound information generated by the CPU 10 are respectively outputted to the display 14 and the speaker 15.

The embodiments use as an example of an operating system (OS) for the electrocardiogram display device 100 a Microsoft Corporation's Windows (registered trademark) XP, NT, 2000, 98SE, ME, CE or the like. The control program for the embodiments works in conjunction with the OS to provide the respective functions. However, the invention is not limited to such embodiments, but the control program alone may provide such functions.

The "electrocardiogram" in the descriptions of the embodiments can be obtained as a result of measurement of the difference in cardiac electric potential between two points on the patient's body. Thus, expressions such as "measurement for an electrocardiogram" as used in the descriptions of the embodiments imply measurement of a cardiac electric potential and the like.

3. Correspondence Between Terms Used in Claims and Embodiments

The correspondence between the terms used in the claims and the embodiments is as follows:

The term "data" refers to electrocardiogram measurement data in the embodiments. The term "output region" refers to a display area for an electrocardiogram in the display 14 in the embodiments.

Figure 8:
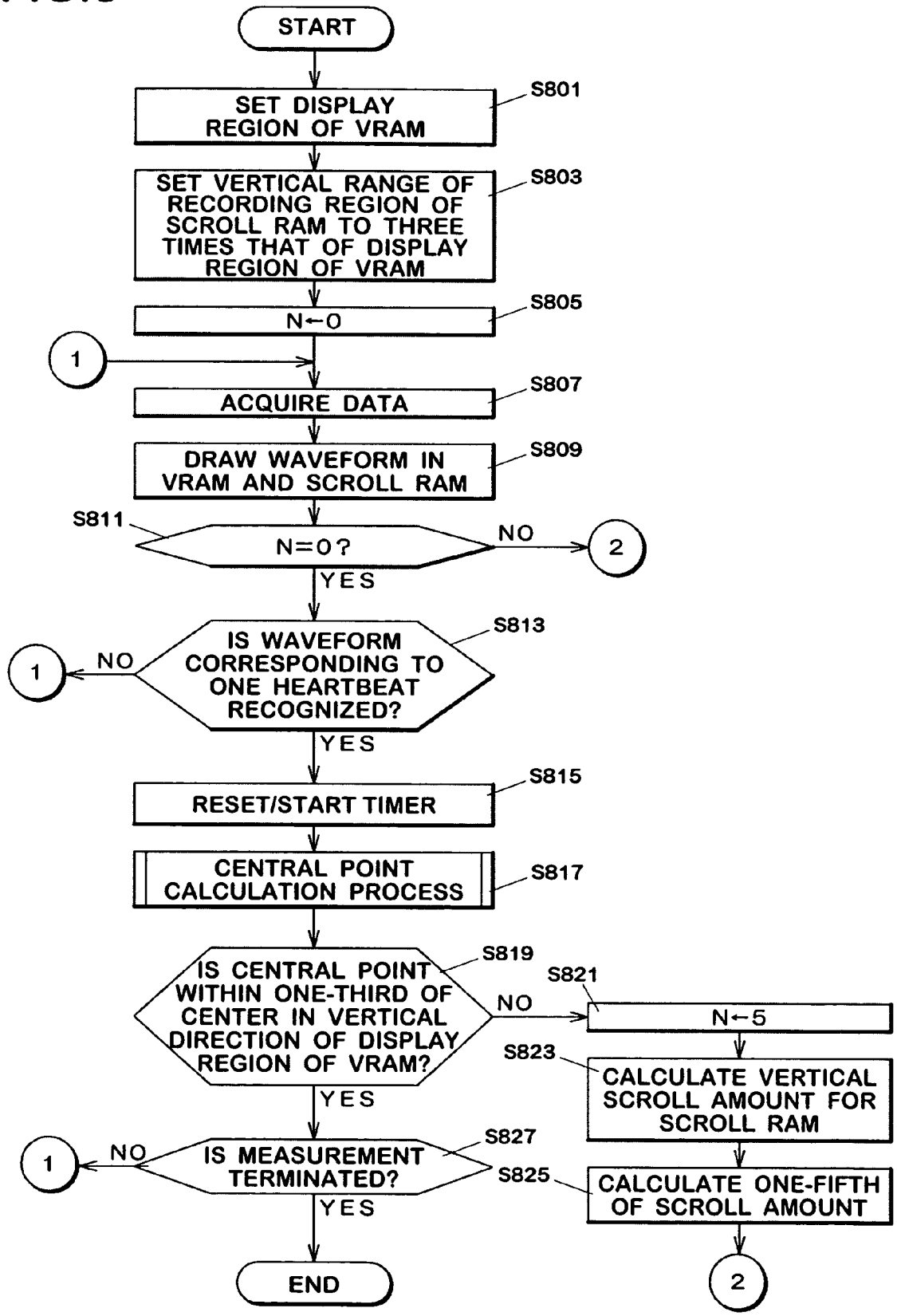
FIG. 8 is a flowchart of the scroll process.
Figure 13:
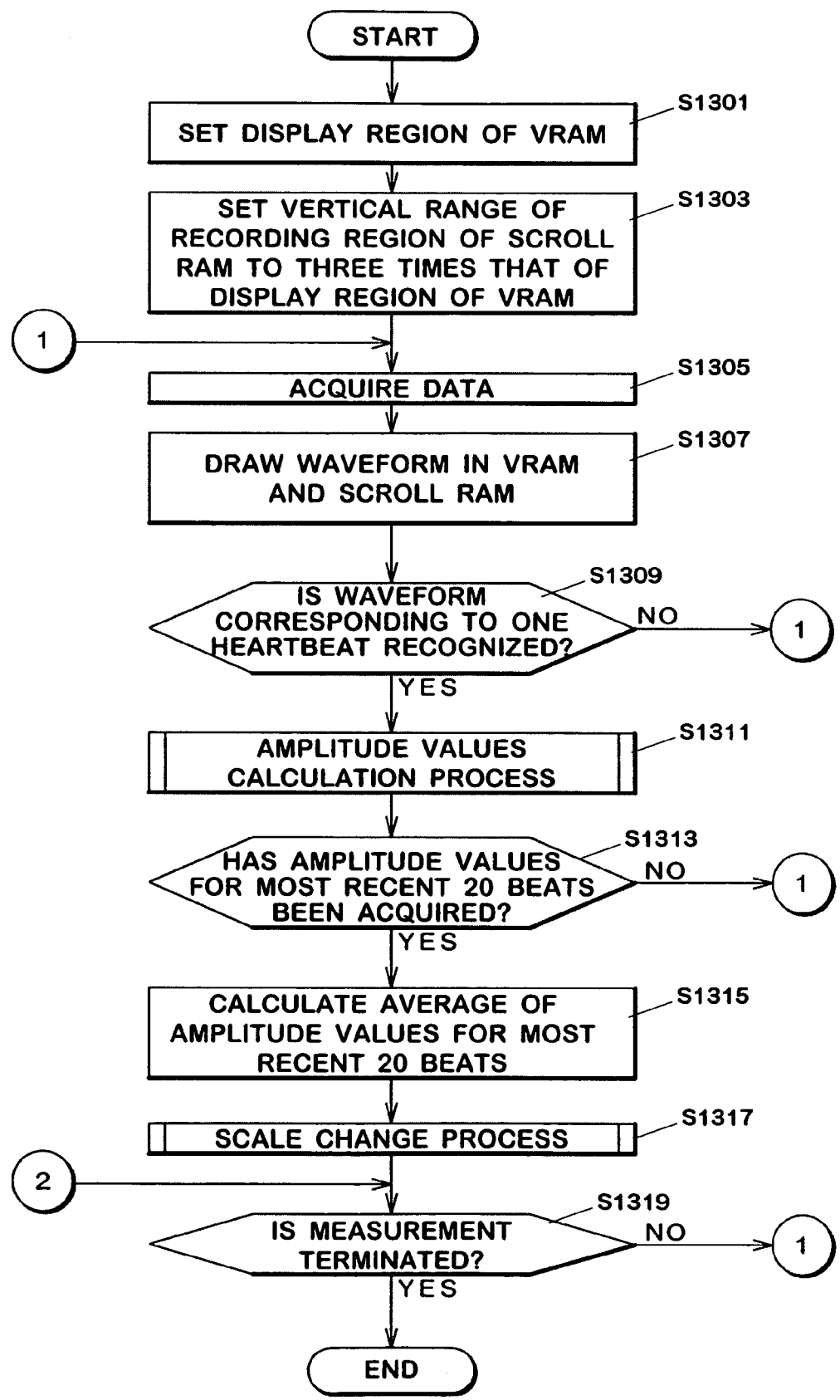
FIG. 13 is a flowchart of the scale change process according to the second embodiment.

The term "data for an object cycle" refers to data on recognition points of a waveform corresponding to one heartbeat recognized (extracted) by the CPU 10 in step S813 of FIG. 8 or step S1309 of FIG. 13 in the embodiments. The term "central portion data" refers to data indicating central points in step S1007, S1011, or S1015 of FIG. 10 in the embodiments. The term "cycle determination means" involves the general concept including a subject with a function of determining an object cycle based on the periodicity of data, and refers, for example, to the CPU 10, which performs a process of step S813 of FIG. 8 or of step S1309 of FIG. 13 in the embodiments. The term "display control means (graph output means)" involves the general concept including a subject with a function of outputting a graph, and refers, for example, to the CPU 10, which performs a process of step S809 of FIG. 8 or of step S1307 of FIG. 13 in the embodiments. The term "display control means (graph position determination means)" involves the general concept including a subject with a function of determining the display position of a graph, and refers, for example, to the CPU 10, which performs a process of step S817, S819 of FIG. 8 in the embodiments. The term "display control means (graph position correction means, display position correction process)" involves the general concept including a subject with a function of correcting the display position of a graph, and refers, for example, to the CPU 10, which performs a process of step S903, S905 of FIG. 9 in the embodiments.

Figure 14:
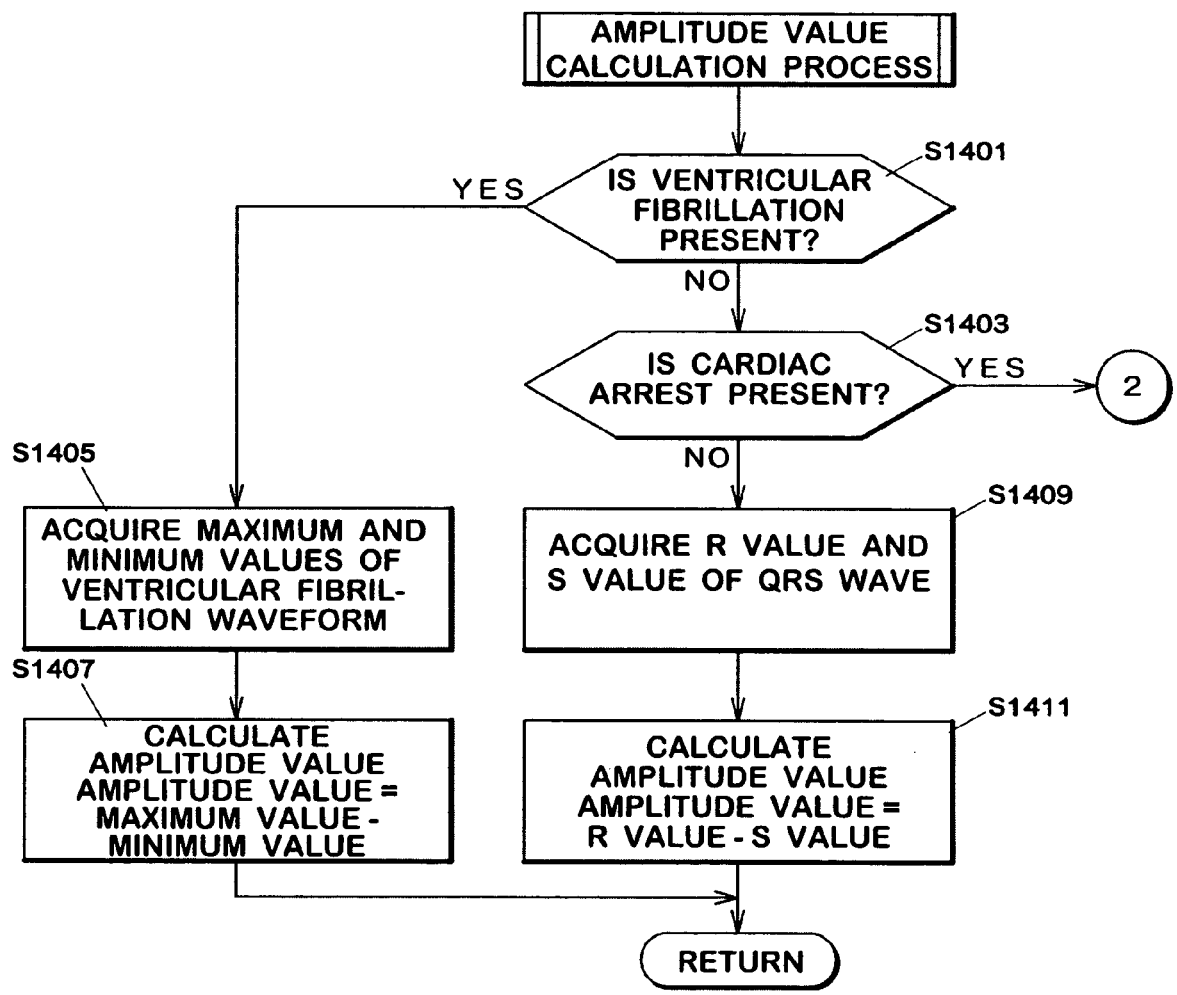
FIG. 14 is a flowchart of the scale change process according to the second embodiment.

The term "amplitude in a cycle" refers to the difference between an R value and an S value in a QRS wave (refer to S1411 of FIG. 14), or the difference between a maximum and a minimum in a ventricular fibrillation waveform (refer to S1407 of FIG. 14). The term "amplitude data" refers to data indicating amplitude values in step S1411 or step S1407 of FIG. 14 in the embodiments. The term "display control means (amplitude data determination means)" involves the general concept including a subject with a function of determining amplitude data, and refers, for example, to the CPU 10, which performs a process of step S1311, S1313, S1315 of FIG. 13 in the embodiments. The term "display control means (scale change means)" involves the general concept including a subject with a function of changing the scale, and refers, for example, to the CPU 10, which performs a process of step S1317 of FIG. 13 in the embodiments.

The terms "first recording region" and "second recording region" respectively refer to the VRAM 22 and the scroll RAM 24 of FIG. 2 in the embodiments.

4. Outline of Electrocardiographic Waveform

Electrocardiogram measurement data to be processed by the CPU 10 of the electrocardiogram display device 100 will be described with reference to the drawings.

4-1. Electrocardiographic Waveform

Figure 3:
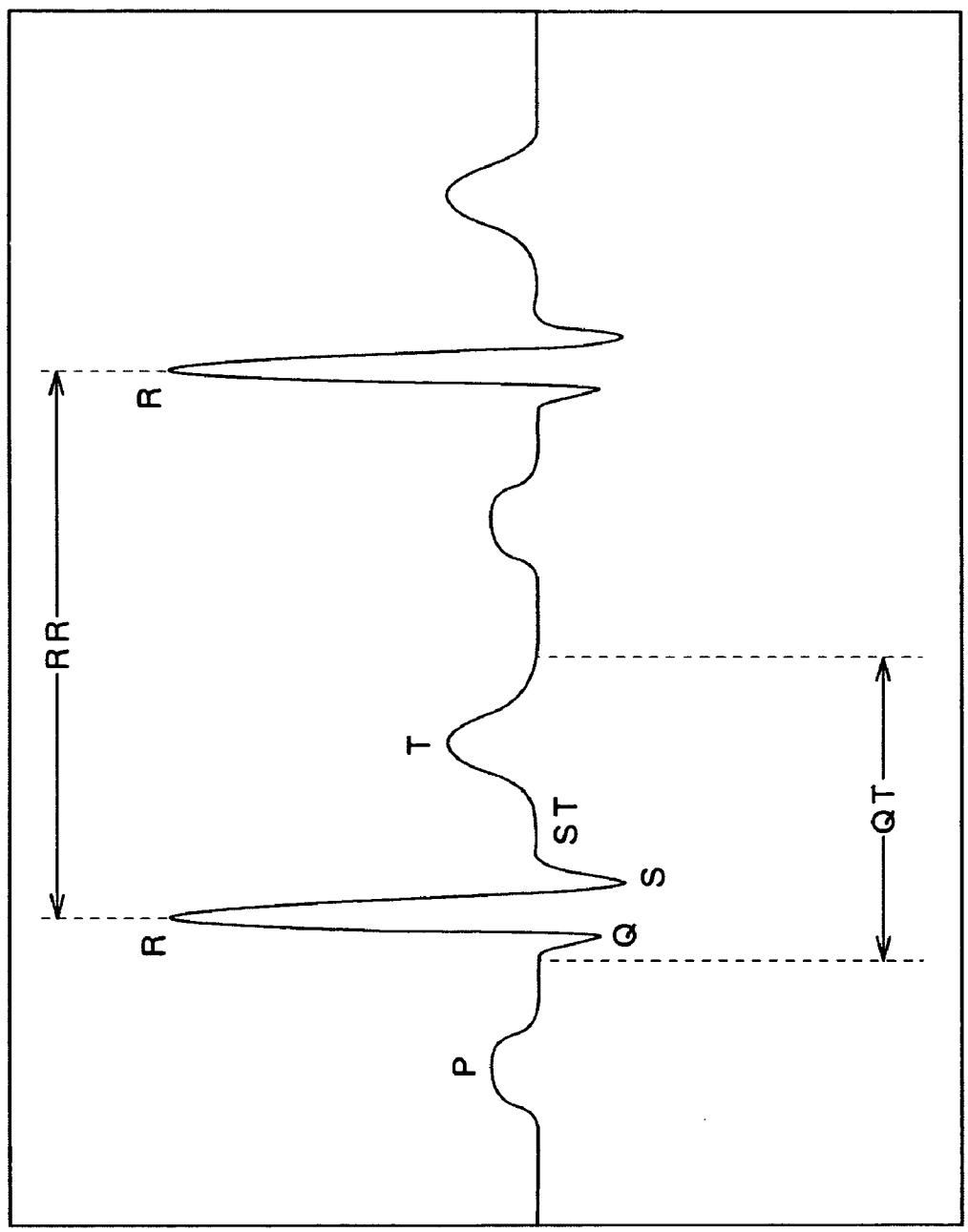
FIG. 3 shows recorded electrocardiographic waveform data represented schematically in the form of a graph.

The CPU 10 continuously records digital data (electrocardiographic waveform data) obtained via the ECG electrodes 20 in the memory 16 (or the F-ROM 17) for each of the 12 leads. FIG. 3 shows electrocardiographic waveform data recorded for one of the leads, represented schematically in the form of a graph (vertical axis: electric potential (voltage), horizontal axis: time). The CPU 10 performs a process of drawing an electrocardiographic waveform such as shown in FIG. 3 on the display 14. An electrocardiogram is drawn by moving the plot point (in the right direction on the display) as the measurement time for the electrocardiogram elapses. The CPU 10 also recognizes a waveform corresponding to each heartbeat based on the electrocardiogram measurement data.

As shown in FIG. 3, the CPU 10 recognizes (extracts), from the electrocardiographic waveform, all or part of a P (P potential or P-wave height), a Q (Q potential or Q-wave height), an R (R potential or R-wave height), an S (S potential or S-wave height), a T (T potential or T-wave height), an ST (ST level), a QT (QT interval), and an RR (RR interval), as recognition value data (characteristics) to record them in the memory 16 (or the F-ROM 17). When the shape of a waveform is normal, the CPU 10 recognizes each heartbeat and the various waves in the electrocardiogram, for example by a process as follows:

(1) Recognition of One Heartbeat: After sampling electrocardiographic waveform data (electric potential or voltage values) for a predetermined period of time, the CPU 10 recognizes an R-wave, which is a local maximum component exceeding a prescribed threshold, and a next R-wave (which is a local maximum component exceeding the prescribed threshold), and recognizes an RR interval as one heartbeat. At this time, T-wave components, which are local maximums other than the R-waves (with frequencies lower than those of the R-waves), may be removed using a low-cut filter.

(2) P-wave: A local maximum which appears 200-300 msec before an R-wave is recognized as a P-wave.

(3) Q-wave: A local minimum which appears immediately before an R-wave is recognized as a Q-wave.

(4) S-wave: A local minimum which appears immediately after an R-wave is recognized as an S-wave.

(5) T-wave: A local maximum which appears between an R-wave and a next R-wave is recognized as a T-wave.

(6) ST-segment: When a linear interpolation is performed between an S-wave and a T-wave on the electrocardiogram, a portion which appears as a local maximum component between them is recognized as an ST-segment.

Occasionally, high-frequency noises with abnormal cycles may appear in an electrocardiogram of a patient and extraction of recognition value data cannot be made precisely, depending on the motion of the patient during measurement of the electrocardiogram. As a method for removing such high-frequency noises and obtaining precise recognition value data, a technique disclosed in JP-A-Hei 6-261871, for example, may be used.

4-2. Central Point and Amplitude of Electrocardiographic Waveform

Figure 4:
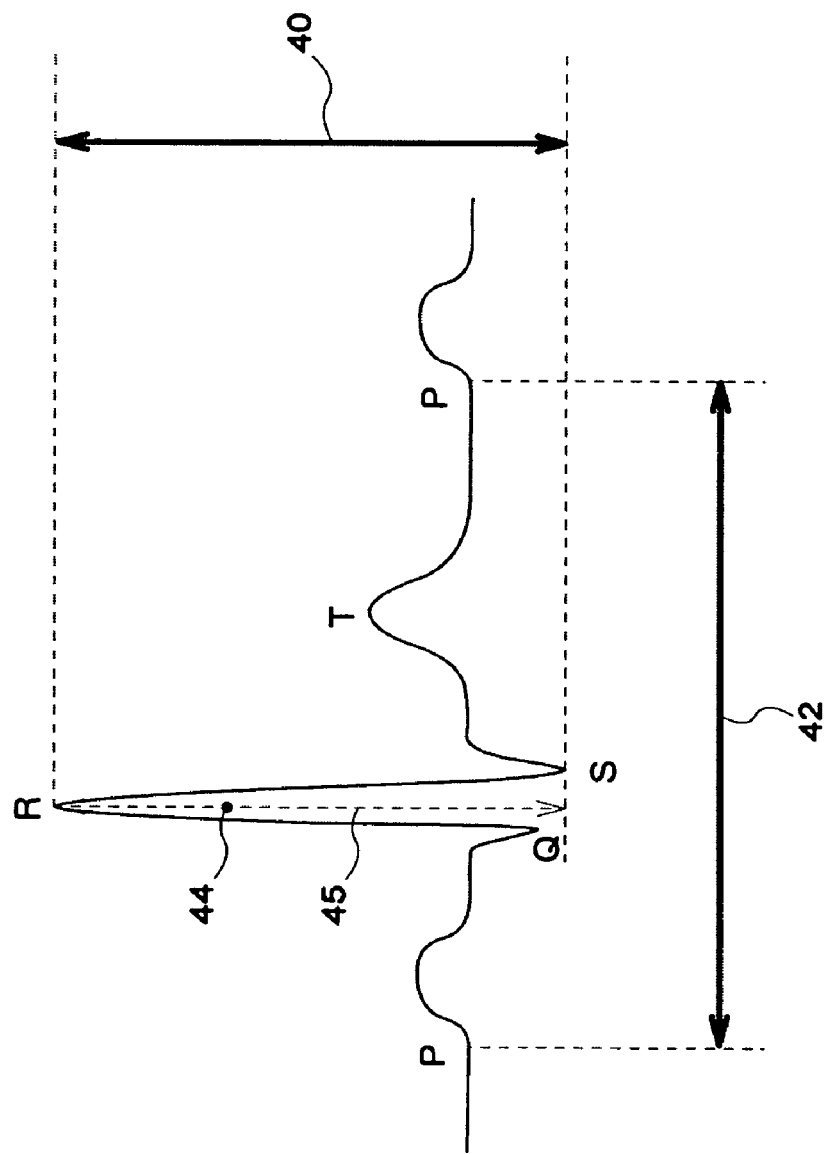
FIG. 4 is a schematic diagram showing the position of a central point and the amplitude of an electrocardiographic waveform calculated by a CPU of the electrocardiogram display device.

FIG. 4 illustrates central point data and amplitude data on an electrocardiogram utilized by the CPU 10 in the first and second embodiments.

In FIG. 4, a PP interval 42 (between two P-waves) is defined as one heartbeat (a cardiac cycle). The CPU 10 finds data indicating a point 44 on a line 45 connecting an R-wave and an S-wave on the electrocardiographic waveform (a vertical line on the display 14) and one-third the way down from the highest point, as central point data (refer to step S1011 of FIG. 10). In other words, the point 44 divides an R-S segment at a ratio of 1:2 ("divides a segment between an R-wave height and an S-wave height at a ratio of 1:2"). The central point data on the point 44 is utilized in the first embodiment (scroll process).

Depending on the condition of the patient's heart, the waveform may have a less R-wave height, which may rather be approximately as high as a Q-wave height, and a low S-wave height. Even in such cases, a point dividing a segment between an R-wave and an S-wave at a ratio of 1:2 is found as central point data through step S1011 of FIG. 10.

The CPU 10 also finds an RS difference 40, which is the difference in electric potential (difference in amplitude)

between an R and an S, as amplitude data. The amplitude data on the RS difference 40 is utilized in the second embodiment (scale change process).

Figure 5:
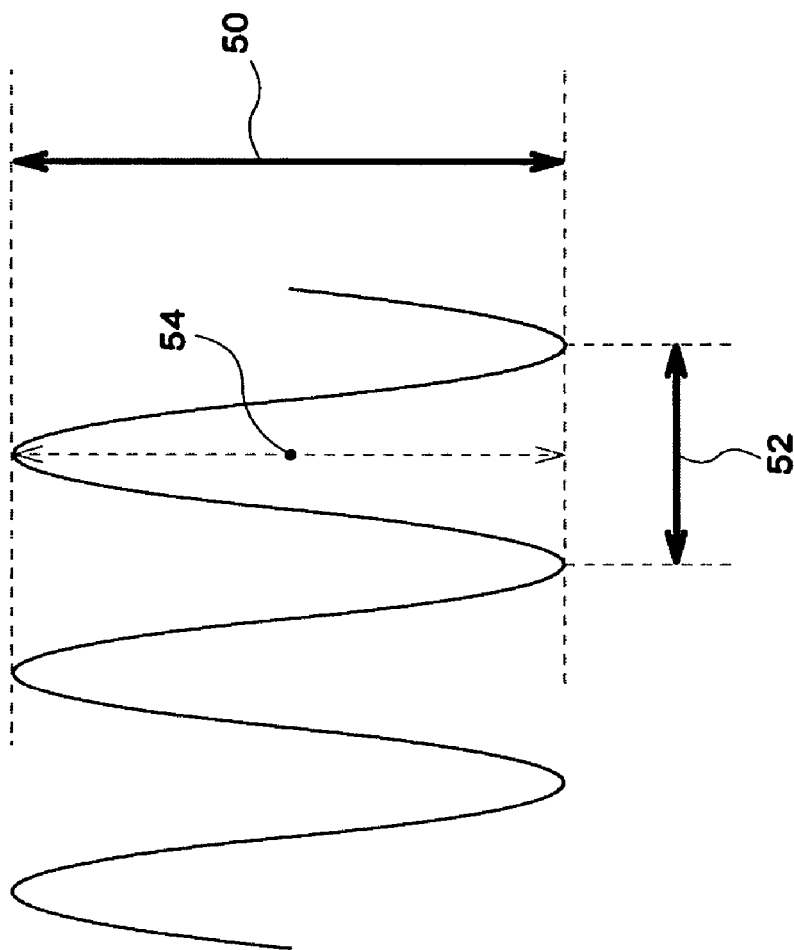
FIG. 5 is a schematic diagram showing the position of a central point and the amplitude of an electrocardiographic waveform calculated by the CPU of the electrocardiogram display device where the electrocardiographic waveform is a ventricular fibrillation waveform.

4-3. Central Point and Amplitude of Electrocardiographic Waveform of Ventricular Fibrillation FIG. 5 illustrates central point data and amplitude data on an electrocardiogram when ventricular fibrillation (and/or ventricular flutter (hereinafter the same)) is occurring. When ventricular fibrillation is occurring, an electrocardiogram generally draws a sine wave, not a normal electrocardiographic waveform. Thus, in the embodiments, a different technique is used from that used in the case of FIG. 4 to calculate central point data or the like, in cases of ventricular fibrillation.

In FIG. 5, one cycle interval 52 of the sine wave corresponds to one heartbeat. The CPU 10 finds data indicating a point 54, which is a central point of a line (a vertical line on the display 14) connecting a maximum point and a minimum point in one heartbeat ("a local maximum or a local minimum in each cycle"), as central point data. The central point data on the point 54 is utilized in the first embodiment (scroll process).

The CPU 10 also finds an difference 50, which is the difference in electric potential (difference in amplitude) between the maximum value and the minimum value, as amplitude data. The amplitude data on the difference 50 is utilized in the second embodiment (scale change process).

The scroll process in the first embodiment is performed with respect to the vertical direction (Y-axis direction) of the display 14. Thus, the calculation of the central point data as described above may utilize data indicating points in the Y-axis direction such as, for example, voltage values (mV). However, the scroll process may be performed also in consideration of the horizontal direction (X-axis direction) of the display 14, in which case the calculation of the central point data may utilize positional data in both directions of the X-axis (time data) and the Y-axis (voltage data) (for convenience of illustration, in FIG. 4 and FIG. 5, the position of a central point is defined in both X-axis and Y-axis directions).

5. First Embodiment (Scroll Process)

Now, details of a program for the scroll process according to the first embodiment are described with reference to FIG. 7, followed by details of a process performed by the CPU 10 of the electrocardiogram display device 100 made with reference to flowcharts of the program shown in FIG. 8-FIG. 10 and the like.

5-1. Details of Scroll Process

FIG. 7 schematically shows the correspondence between the VRAM 22 and the scroll RAM 24 in the course of the scroll process.

The VRAM 22 is a memory (buffer) that screen contents to be presented on the display 14 are recorded. Thus, electrocardiogram measurement data recorded in the VRAM 22 is converted into a display signal and outputted to a display area of the display 14. On the other hand, the scroll RAM 24, also a memory (buffer) that screen contents are recorded, does not allow electrocardiogram measurement data recorded therein to be directly displayed on the display area as the VRAM 22 does, but is utilized by the CPU 10 to perform a scroll process on the screen contents from the electrocardiogram measurement data (i.e., functions as a virtual VRAM).

More specifically, the CPU 10 writes acquired electrocardiogram measurement data into both the VRAM 22 and the scroll RAM 24 as a graph. Normally, the CPU 10 outputs the electrocardiogram as the recorded contents of the VRAM 22 to the display area of the display 14. If the recognized electrocardiographic waveform corresponding to the most recent heartbeat does not fall within the display area of the display 14, the CPU 10 scrolls the recorded contents of the scroll RAM 24 and duplicates (copies) the recorded contents after the scroll process to the VRAM 22. As a result, the electrocardiogram on the display 14 is scrolled.

Figures 7A, 7B:
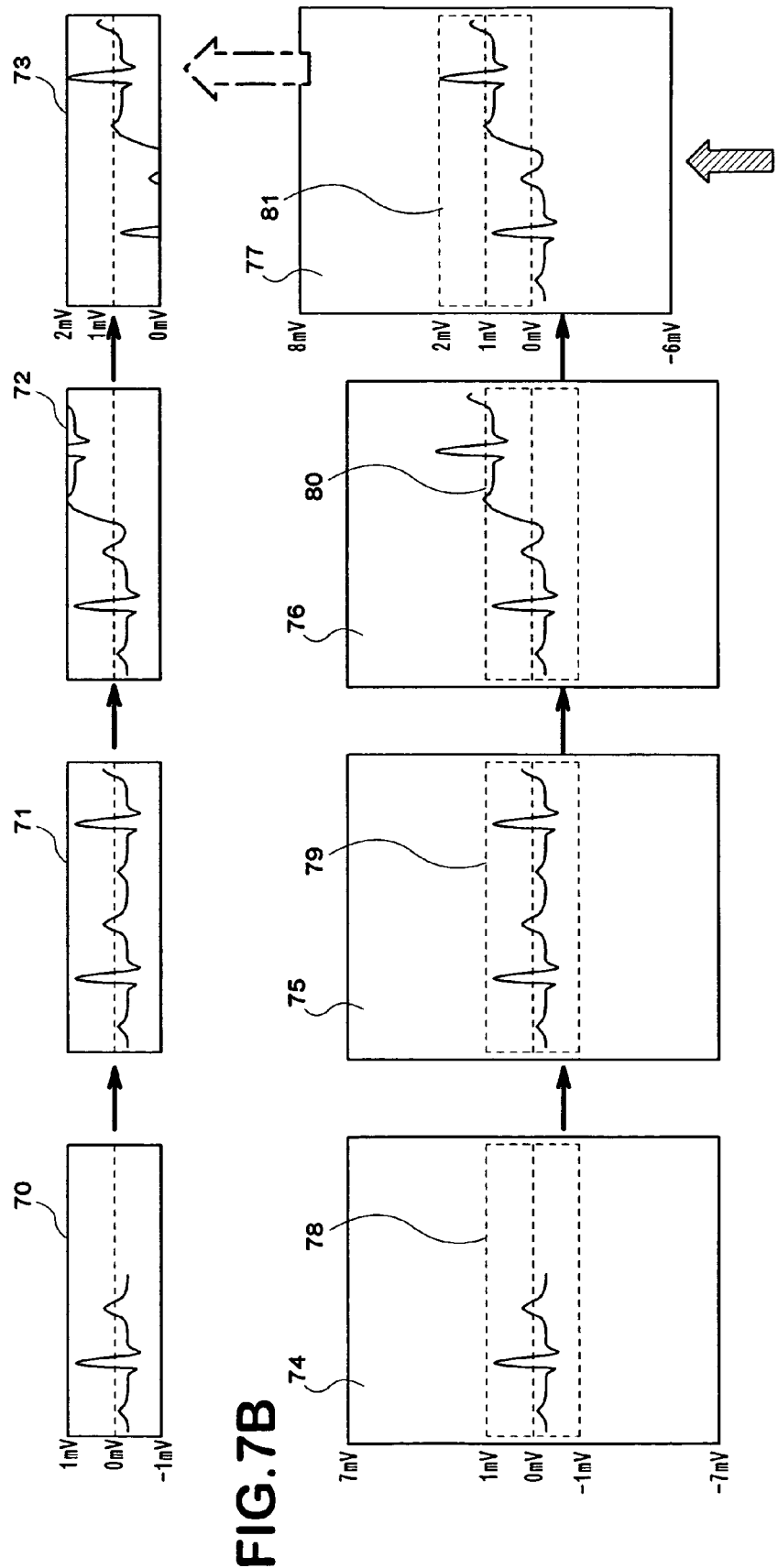
FIG. 7A and FIG. 7B are conceptual diagrams showing the correspondence between a VRAM and a scroll RAM during the scroll process.

FIG. 7 shows schematic representations of the recorded contents of the VRAM 22 and the scroll RAM 24, as screen contents. FIG. 7A shows chronological changes in the recorded contents of the VRAM 22, and FIG. 7B shows chronological changes in the recorded contents of the scroll RAM 24.

The recorded contents of the VRAM 22 correspond to a display region of a width from −1 mV to 1 mV along the vertical axis, while the recorded contents of the scroll RAM 24 correspond to a display region of a width from −7 mV to 7 mV along the vertical axis. Coordinate information on these recorded contents along the vertical axis is defined by an upper limit, a lower limit, and a median. The recorded contents of both the VRAM 22 and the scroll RAM 24 correspond to a full display region of a time span of five seconds along the horizontal axis. In this embodiment, a measured display area for an electrocardiogram on the display 14 may have rates of 1 mV=1 centimeter (cm) along the vertical axis and 1 second=25 millimeters (mm) along the horizontal axis.

Now, details of the scroll process are described based on FIG. 7. The CPU 10 writes electrocardiogram measurement data into both the VRAM 22 and the scroll RAM 24. As a result, data 70 is recorded in the VRAM 22 while data 74 is recorded in the scroll RAM 24. The contents recorded in the VRAM 22 are displayed in the display area of the display 14 (hereinafter the term "display 14" should imply the display area of the display 14). The recorded contents of a central portion 78 of the scroll RAM 24 are the same as the data 70 in the VRAM 22. The central portion 78 may be defined, for example, by coordinate information on a vertical median of the scroll RAM 24 and vertical width information with respect to the vertical median.

As time elapses, the CPU 10 additionally writes new electrocardiogram measurement data into the VRAM 22 and the scroll RAM 24. As a result, data 71 is recorded in the VRAM 22 and data 75 is recorded in the scroll RAM 24 (a central portion 79 corresponds to the data 71).

The CPU 10 additionally writes new electrocardiogram measurement data into the VRAM 22 and the scroll RAM 24. Data 72 is recorded in the VRAM 22 and data 76 is recorded in the scroll RAM 24 (a central portion 80 corresponds to the data 72). At this time, the CPU 10 determines that the waveform of a heartbeat at the right end is not presented on the display 14 as shown by the data 72, and performs a scroll process using the scroll RAM 24. A determination as to whether or not a scroll process is required is made in the same manner as described in the section of "1-1. Outline of Scroll Process (First Embodiment)."

The CPU 10 performs a scroll process on the recorded contents of the scroll RAM 24 to create data 77. Specifically, in FIG. 7B, the recording region of the scroll RAM 24 is changed from a range from −7 mV to 7 mV to a range from −6 mV to 8 mV. In association with the change, a central portion 81, correlated with the recorded contents of the VRAM 22, will be changed to a range from 0 mV to 2 mV. Specifically, the recorded contents of the scroll RAM 24 are erased, the respective coordinates of an upper limit, a lower limit and a median in the vertical direction are changed by a predetermined number of units (for example, number of pixels), and then redrawing (rewriting) is performed. In this manner, the correlation between the coordinate information on the scroll RAM 24 and the electric potential values (mV) of the electrocardiogram measurement data is changed. For a program that performs such a scroll process, scroll functions such as ScrollWindow or ScrollDC, for example, may be used.

The CPU 10 copies (duplicates) the recorded contents of the central portion 81 to the VRAM 22, to allow data 73 to be recorded in the VRAM 22. As a result, a scrolled electrocardiogram will be presented on the display 14. With this copying, the correlation between the coordinate information on the VRAM 22 and the electric potential values (mV) of the electrocardiogram measurement data is also changed. In the example of FIG. 7, the central value of the VRAM 22 is changed from 0 mV to 1 mV. Thus, an electrocardiogram based on the electrocardiogram measurement data acquired after the scroll process is drawn in continuity with the electrocardiogram after the scroll process.

When the electrocardiogram is displayed up to the right end of the display region of the VRAM 22, that is, when five seconds have passed since the display of the electrocardiogram appeared, electrocardiogram measurement data is recorded again from the left end of the display region of the VRAM 22.

5-2. Description of Scroll Process

Figure 9:
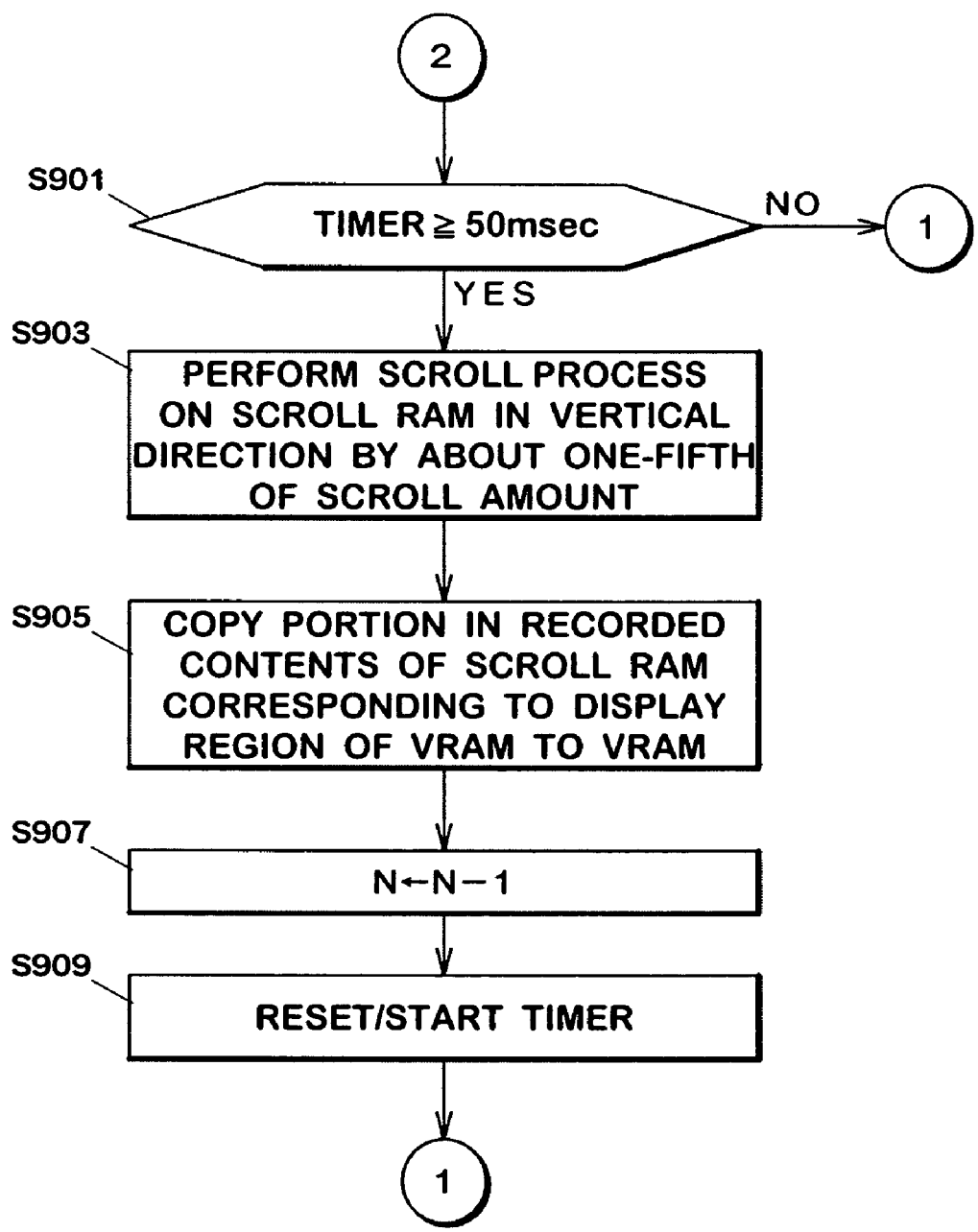
FIG. 9 is a flowchart of the scroll process.
Figure 10:
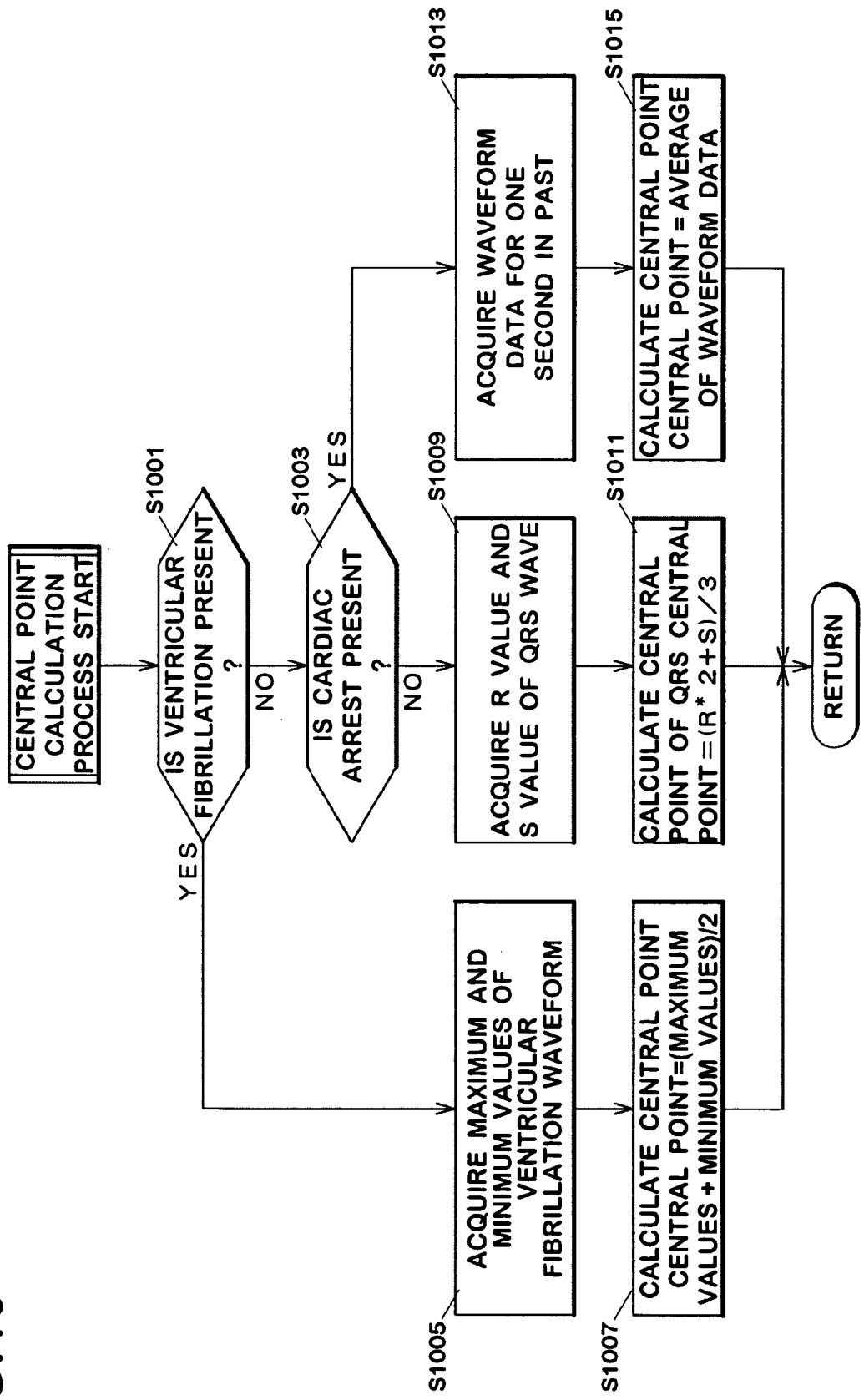
FIG. 10 is a flowchart of the scroll process.

With reference to flowcharts of a program shown in FIG. 8-FIG. 10 and the like, details of a program for the scroll process performed by the CPU 10 of the electrocardiogram display device 100 are described.

The sampling frequency of electrocardiogram measurement data inputted through AD conversion may be set to, for example, 125, 250, 500 or 1000 Hz. The CPU 10 of the electrocardiogram display device 100 draws on the display 14 (writes into the VRAM 22) electrocardiogram measurement data sampled at the specified frequency. At this time, a predetermined number of pieces of sampled data may be grouped into blocks and then be drawn on the display 14.

The CPU 10 may perform the drawing process of an electrocardiogram on the display 14, and the scroll process according to the first embodiment or the scale change process according to the second embodiment, either at different time points (or at different time intervals) or at the same time point (at the same time intervals).

Descriptions of two cases will be made below, namely a case where no scroll process is performed during the drawing of an electrocardiogram, and a case where a scroll process is performed during the drawing of an electrocardiogram, for convenience of description.

5-3. Case where No Scroll Process is Performed during Drawing of Electrocardiogram The CPU 10 sets a display region of the VRAM 22, where screen contents to be presented on the display 14 are recorded (step S801 of FIG. 8). Specifically, the CPU 10 sets coordinate information on the display region such that its vertical axis corresponds to a range from −1 mV to 1 mV and its horizontal axis corresponds to a range of five seconds. The CPU 10 sets the vertical range of a recording region of the scroll RAM 24 to three times (from −7 mV to 7 mV) that of the display region of the VRAM 22 (step S803).

The CPU 10 sets a "loop value" N representing the loop count of the scroll process, to be described later, to "0" (step S805). The CPU 10 measures a 12-lead electrocardiographic waveform via the ECG electrodes 20 attached to the patient's body and the amplifier 11, to record electrocardiogram measurement data to the memory 16 (step S807) (data acquisition means). A 12-lead electrocardiogram is an electrocardiogram including twelve patterns obtained from several to a dozen electrodes attached to a living body. Based on the acquired electrocardiogram measurement data, the CPU 10 records (draws) screen contents (electrocardiogram) for presentation on the display 14 to the VRAM 22 and the scroll RAM 24 (step S809) (graph output means).

The CPU 10 determines whether or not "N=0" holds true (step S811), and if it is determined that "N=0" holds true, determines whether or not a waveform corresponding to one heartbeat has been recognized (extracted) (step S813). Specifically, the determination in step S813 is made based on whether or not data (recognition value data) on respective recognition points (P-wave, Q-wave, R-wave, S-wave and T-wave) between a P-wave starting a cardiac cycle and a P-wave starting a next cardiac cycle has been extracted. If it is determined in step S813 that a waveform corresponding to one heartbeat has not been recognized, the CPU 10 repeats the processes in and after step S807.

On the other hand, if it is determined in step S813 that a waveform corresponding to one heartbeat has been recognized, the CPU 10 resets a scroll timer and then starts the timer (step S815). In step S813, in case of cardiac arrest (death), a P-wave and the like are not recognized. Therefore, after electrocardiogram measurement data (normally, data to be displayed as a flat electrocardiogram) is acquired for one second, the CPU 10 performs the process of step S815. The CPU 10 calculates a central point of the waveform corresponding to one heartbeat recognized in step S813 (step S817). Details of the central point calculation process will be described later.

The CPU 10 determines whether or not the central point found in step S817 is positioned within one-third of the center (a central region in an output region) in the vertical direction of the display region of the VRAM 22 (refer to step S801) (step S819). Specifically, the CPU 10 determines whether or not the value for the central point calculated in step S817 is within a range from −0.3 mV to +0.3 mV. If it is determined that the central point is positioned within one-third of the center in the vertical direction of the display region of the VRAM 22, the CPU 10 determines in step S827 whether or not the measurement is terminated. If the measurement is not terminated, the CPU 10 repeats the processes in and after step S807. On the other hand, if the measurement is terminated, the CPU 10 terminates the process. The determination as to whether or not the measurement is terminated may be made based on reception of a user input of information indicating termination of a measurement, absence of an input of electrocardiogram measurement data into the memory, or the like.

The above has described a case where no scroll process is performed during the drawing of an electrocardiogram.

5-4. Case where Scroll Process is Performed during Drawing of Electrocardiogram

Now, a description is made of a case where a scroll process is performed during the drawing of an electrocardiogram.

A case where a scroll process is performed refers to a case where the CPU 10 determines in step S819 that the central point is not positioned within one-third of the center in the vertical direction of the display region of the VRAM 22. In this case, the CPU 10 sets the "loop value" N representing the loop count of the scroll process to "5" (step S821). The CPU 10 calculates a vertical scroll amount for the scroll RAM 24 (step S823). The scroll amount is calculated by an arithmetic expression as follows: (the value for the central point calculated in step S817)−(the vertical median of the display region of the scroll RAM 24) (by finding the difference between the two values). The CPU 10 calculates one-fifth of the scroll amount calculated in step S823 (step S825).

The CPU 10 determines whether or not the scroll timer, which was started in step S815, has reached 50 msec or longer (step S901 of FIG. 9). If the scroll timer has not reached 50 msec or longer, the CPU 10 performs the processes of steps S807 and S809 of FIG. 8, that is, records successively acquired electrocardiogram measurement data in the VRAM 22 and the scroll RAM 24. At this time, since the setting shows N=5, the CPU 10 performs the process of step S901 after step S811. Thus, newly acquired electrocardiogram measurement data is recorded in the VRAM 22 and an electrocardiogram is continuously drawn on the display 14, until the scroll timer indicates that 50 msec or longer has elapsed.

If it is determined in step S901 that the scroll timer indicates that 50 msec or longer has elapsed, the CPU 10 performs a scroll process on the scroll RAM 24 in the vertical direction by one-fifth of the scroll amount calculated in step S825 (step S903).

Specifically, the recorded contents of the scroll RAM 24 are erased, the respective coordinates of an upper limit, a lower limit and a median in the vertical direction are changed by a predetermined number of units (for example, number of pixels), and then redrawing is performed. In this manner, the correlation between the coordinate information on the scroll RAM 24 and the electric potential values (mV) of the electrocardiographic waveform is changed (see the section of "5-1. Details of Scroll Process").

The CPU 10 copies a central portion in the recorded contents of the scroll RAM 24 (a portion to be correlated with the display region of the VRAM 22) to the VRAM 22 (step S905). This process allows the display 14 to present a scrolled electrocardiogram. The CPU 10 sets the loop value "N" to "N−1" (step S907). Specifically, the N, which was set to "5" in step S821 of FIG. 8, is changed to "4" in step S907.

The CPU 10 resets/starts the scroll timer (step S909), and repeats the processes in and after step S807. The CPU 10 performs the above processes constituting a scroll process until N=0 becomes true, to eventually complete the scroll process on an object heartbeat (recognized heartbeat) with a total of five scroll processes. If it is determined in step S811 of FIG. 8 that N=0 holds true, the CPU 10 performs the processes in and after step S813, where the CPU 10 recognizes a next waveform corresponding to one heartbeat. The CPU 10 repeats the above processes until it is determined in step S827 that the measurement is terminated, and if it is determined that the measurement is terminated, terminates the process.

In this embodiment, the loop count is set to 5 in step S821 and one-fifth of the scroll amount is calculated in step S825, because of the purpose of allowing a user to view the course of the scroll process (smooth scroll process). Specifically, in this embodiment, one scroll process is performed when the timer indicates that 50 msec or longer has elapsed in the process of step S901. Since the loop count is set to 5, a necessary scroll process is completed in substantially 250 msec. In this manner, such a necessary scroll process can be presented on the display 14 as divided in five stages, generally allowing recognition of the course of transition of an electrocardiogram by human eyes. A scroll process is completed in 250 msec, because one heartbeat is equivalent to about one second normally, or about 500 msec in cases of a rapid heart rate, and it is necessary to complete a scroll process actually within 500 msec. In this embodiment, for illustration, a scroll process is completed in 250 msec, with a margin.

In step S823 of FIG. 8, the scroll amount may be calculated using respective position values, voltage values (mV), or measured values (mm) in the display region, for central points of the electrocardiographic waveform and the median of the scroll RAM 24, or the like. These values are correlated with each other, and any of the values may be used as a reference in performing an electrocardiogram display process and a scroll process. In this embodiment, for illustration, voltage values are used as a reference in performing calculation of a scroll amount.

The scroll direction in step S903 of FIG. 9 may be defined, for example, as upward if the value of (the value for the central point calculated in step S817)−(the vertical median of the display region of the scroll RAM 24) is positive in the calculation of a scroll amount using voltage values in step S823, and as downward, on the other hand, if the value is negative.

5-5. Flowchart of Central Point Calculation Process

Now, based on FIG. 10, a description is made of details of a program for the central point calculation process performed in step S817 of FIG. 8 as a subroutine.

Data on a central point can be calculated using electric potential (voltage) values for a recognition point such as an R-wave of an electrocardiogram, position values (address values) in the scroll memory 24 corresponding to the position of the recognition point, or measured values in the display region corresponding to the position of the recognition point. In this embodiment, for illustration, electric potential (voltage) values are used in the calculation. Thus, the CPU in this embodiment uses only measurement data acquired in step S807 of FIG. 8 to perform a central point calculation process. However, in another embodiment, a central point calculation process may be performed based on the graphic data on the electrocardiogram drawn (including positional data, etc.).

The CPU 10 of the electrocardiogram display device 100 determines, based on the shape of the electrocardiographic waveform corresponding to one heartbeat recognized in step S813 of FIG. 8, whether or not ventricular fibrillation is present (step S1001 of FIG. 10). If it is determined that ventricular fibrillation is not present, the CPU 10 determines whether or not cardiac arrest is present (step S1003). The CPU 10 may make a determination in step S1001 and step S1003, based on the presence or absence of a recognition point (P-wave, Q-wave, R-wave, S-wave or QRS wave) in the electrocardiographic waveform, or based on the magnitude of amplitude of the waveform.

If it is determined in step S1003 that cardiac arrest is not present, the CPU 10 acquires data on an R potential and an S potential of the heartbeat recognized in step S813 (step S1009). The CPU 10 calculates a central point of the QRS wave (step S1011). The central point is calculated based on an "arithmetic expression: (R potential×2 +S potential)/3." This central point is a central point of a normal electrocardiographic waveform and corresponds to the electric potential (a value with respect to the vertical axis) of the point 44 dividing an R-S segment at a ratio of 1:2 in FIG. 4.

On the other hand, if it is determined in step S1001 that ventricular fibrillation is present, the CPU 10 acquires a maximum value (a local maximum in the object cycle) and a minimum value (a local minimum in the object cycle) of the recognized heartbeat (ventricular fibrillation waveform) (step S1005). The CPU 10 calculates a central point of the ventricular fibrillation waveform (step S1007). The central point is calculated based on an "arithmetic expression: (maximum value+minimum value)/2." This central point corresponds to the electric potential (a value with respect to the vertical axis) of the point 54 in FIG. 5, or a central point of a ventricular fibrillation waveform.

If it is determined in step S1003 that ventricular arrest is present, the CPU 10 acquires electrocardiogram measurement data for one second in the past (step S1013), and calculates a central point of the electrocardiogram measurement data (step S1015). The central point is obtained by calculating an average of the electrocardiogram measurement data.

Through the above processes, the CPU 10 calculates a central point respectively for a normal case, a case of ventricular fibrillation and a case of ventricular arrest, and then performs the processes in and after step S819 of FIG. 8.

Details of a program for the scroll process according to the first embodiment have been described above. It should be noted that the descriptions of the program, algorithms or the like of the process are made for illustration purposes. Thus, changes can be made by means known to those skilled in the art, of the techniques for the scroll process (loop count, unit time for the loop, scroll amount, timing to perform a scroll process, etc.), the settings of the size of the display regions of the VRAM and the scroll RAM (refer to steps S801 and S803 of FIG. 8, etc.), the criteria for determining the necessity for a scroll process (refer to step S819 of FIG. 8), and the like.

For example, in the embodiment, the process of recognizing a waveform corresponding to one heartbeat in step S813 of FIG. 8 is performed after the drawing process of step S809; the present invention is not limited thereto, but the drawing process may be performed after the process of recognizing a waveform corresponding to one heartbeat. The scroll process is performed depending on the last (most recent) waveform corresponding to one heartbeat recognized; the present invention is not limited thereto, but it may be performed depending on a waveform corresponding to a heartbeat before the last one (in the past). A point dividing an RS segment at a ratio of 1:2 from the top is used as central point for illustration (refer to step S1011 of FIG. 10), but another point may be adopted. The presence or absence of a scroll process is determined, for illustration, depending on whether or not the central point is within one-third of the center in the vertical direction of the display region of the VRAM 22 (corresponding to "a central region in an output region") (refer to step S819 of FIG. 8); the present invention is not limited thereto, but other criteria may be adopted, such as whether or not the central point is within one-fourth of the center in the vertical direction of the display region of the VRAM 22, whether or not the value for the central point of the electrocardiographic waveform is equal to the value for the central point in the vertical direction of the display region of the VRAM 22, or the like.

5-6. Presentation on Display in First Embodiment (Scroll Process)

Figure 11A:
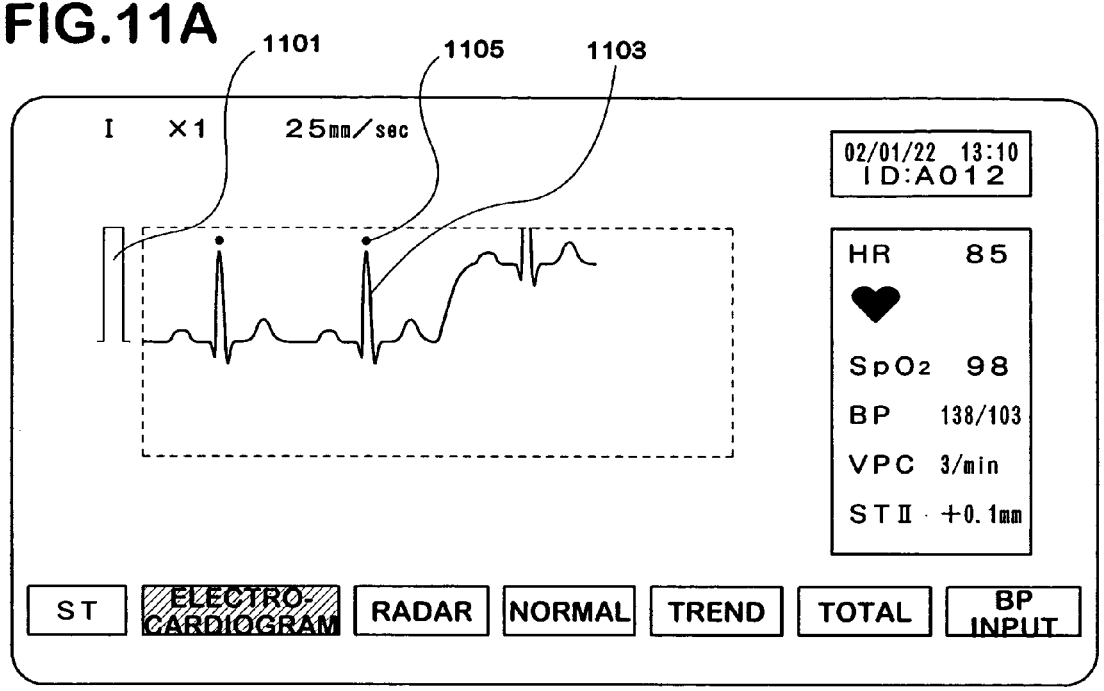
FIG. 11A and FIG. 11B show examples of a presentation on a display of the electrocardiogram display device during the scroll process.

FIG. 11 shows examples of a presentation on the display 14 in the first embodiment. FIG. 11A shows an example of a presentation on the display 14 before the scroll process. The display 14 presents an electrocardiogram 1103, in addition to a recognition point 1105 plotted near an R-wave of each heartbeat. An electrocardiographic waveform criterion 1101, shown on the left side of the electrocardiogram, represents a vertical width corresponding to a voltage of 1 mV.

The electrocardiogram 1103 is displayed in a width from −1 mV to 1 mV. The width from −1 mV to 1 mV represents a width of voltage defined with a center of the vertical axis of a display area for the electrocardiogram set as a virtual zero point (0 mV), and therefore does not always coincide with an electric potential value (an absolute value) for the voltage. In this embodiment, an electric potential value (absolute values) for the voltage is not displayed; however, such a value may be displayed as necessary.

Figure 11B:
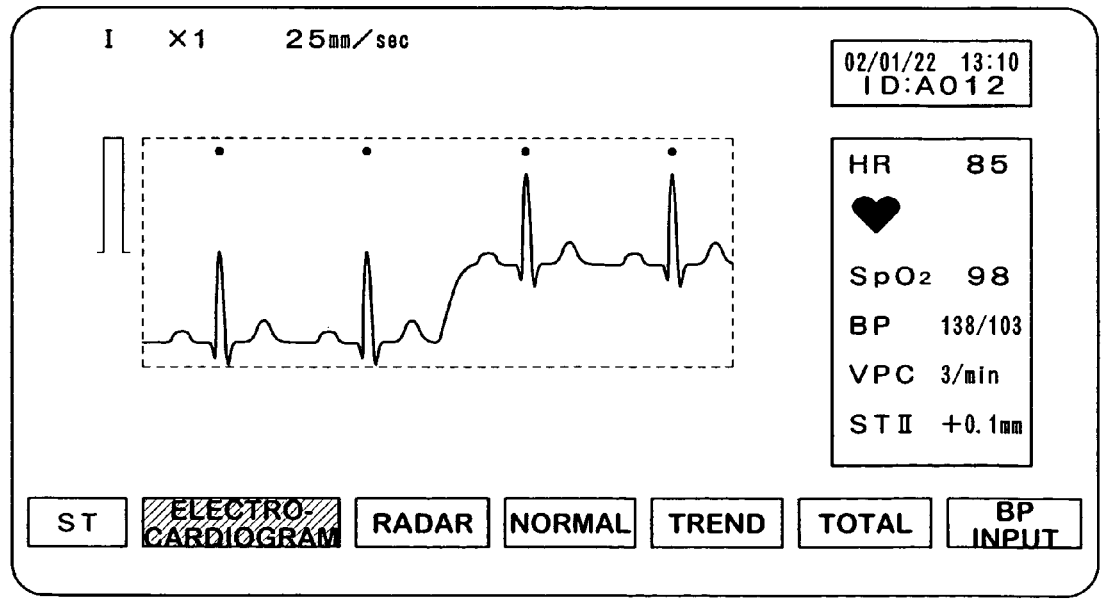

FIG. 11B shows an example of a presentation on the display 14 after the scroll process. As shown in the drawing, the electrocardiogram is moved through the scroll process, to a position that facilitates viewing of the shape of the electrocardiographic waveform.

6. Second Embodiment (Scale Change Process)

Now, details of a program for the scroll process according to the second embodiment are described with reference to FIG. 12, followed by details of a process performed by the CPU 10 of the electrocardiogram display device 100 made with reference to flowcharts of FIG. 13-FIG. 15 and the like.

6-1. Details of Scale Change Process

FIG. 12 schematically shows the recorded contents of the VRAM 22 in the course of the scale change process. FIG. 12 shows schematic representations of the recorded contents of the VRAM 22, as screen contents. Coordinate information and the like on the recorded contents of the VRAM 22 are the same as in FIG. 7.

FIG. 12A shows an example where the recorded contents of the VRAM 22 are compressed. The VRAM 22 has recorded therein data 1201 including an electrocardiogram 1202. An amplitude reference line 1203 is for illustration purposes, and shows half the vertical dimension of a display region of the VRAM 22. Since the amplitude of the electrocardiogram 1202 is larger than half of the vertical dimension of the display area of the VRAM 22, the CPU 10 of the electrocardiogram display device 100 performs a scale change process such that the amplitude of the electrocardiogram 1202 is compressed in the vertical direction. As a result, as shown in the right part of FIG. 12A, the VRAM 22 has recorded therein data 1205 including an electrocardiogram 1206, which is compressed to half in the vertical direction. In other words, the data 1201 recorded in the VRAM 22 is replaced by the data 1205 corresponding to a display region of a width from −2 mV to 2 mV, as a result of compression.

FIG. 12B shows an example where the recorded contents of the VRAM 22 are expanded. The VRAM 22 has recorded therein data 1211 including an electrocardiogram 1212. An amplitude reference line 1213 is for illustration purposes, and shows one-fifth of the vertical dimension of a display region of the VRAM 22. Since the amplitude of the electrocardiogram 1212 is smaller than one-fifth of the vertical dimension of the display area of the VRAM 22, the CPU 10 performs a scale change process such that the amplitude of the electrocardiogram 1212 is expanded in the vertical direction. As a result, as shown in the right part of FIG. 12B, the VRAM 22 has recorded therein data 1215 including an electrocardiogram 1216, which is expanded to double in the vertical direction. In other words, the data 1211 in the VRAM 22 is replaced by the data 1215 corresponding to a display region of a width from −0.5 mV to 0.5 mV, as a result of expansion.

The CPU 10 of the electrocardiogram display device 100 performs a scale change process according to the second embodiment and a scroll process according to the first embodiment in parallel with each other using separate programs. However, the CPU 10 may perform only one of such programs. Specifically, the CPU 10 may be configured to perform an electrocardiogram display process and a scroll process (first embodiment) only, or an electrocardiogram display process and a scale change process (second embodiment) only.

As an alternative to the words "scale change" in the second embodiment, other expressions may be used, such as range change, amplitude correction, display magnification adjustment, display reduction ratio change, enlargement process, or contraction process.

6-2. Description of Scale Change Process

Figure 15:
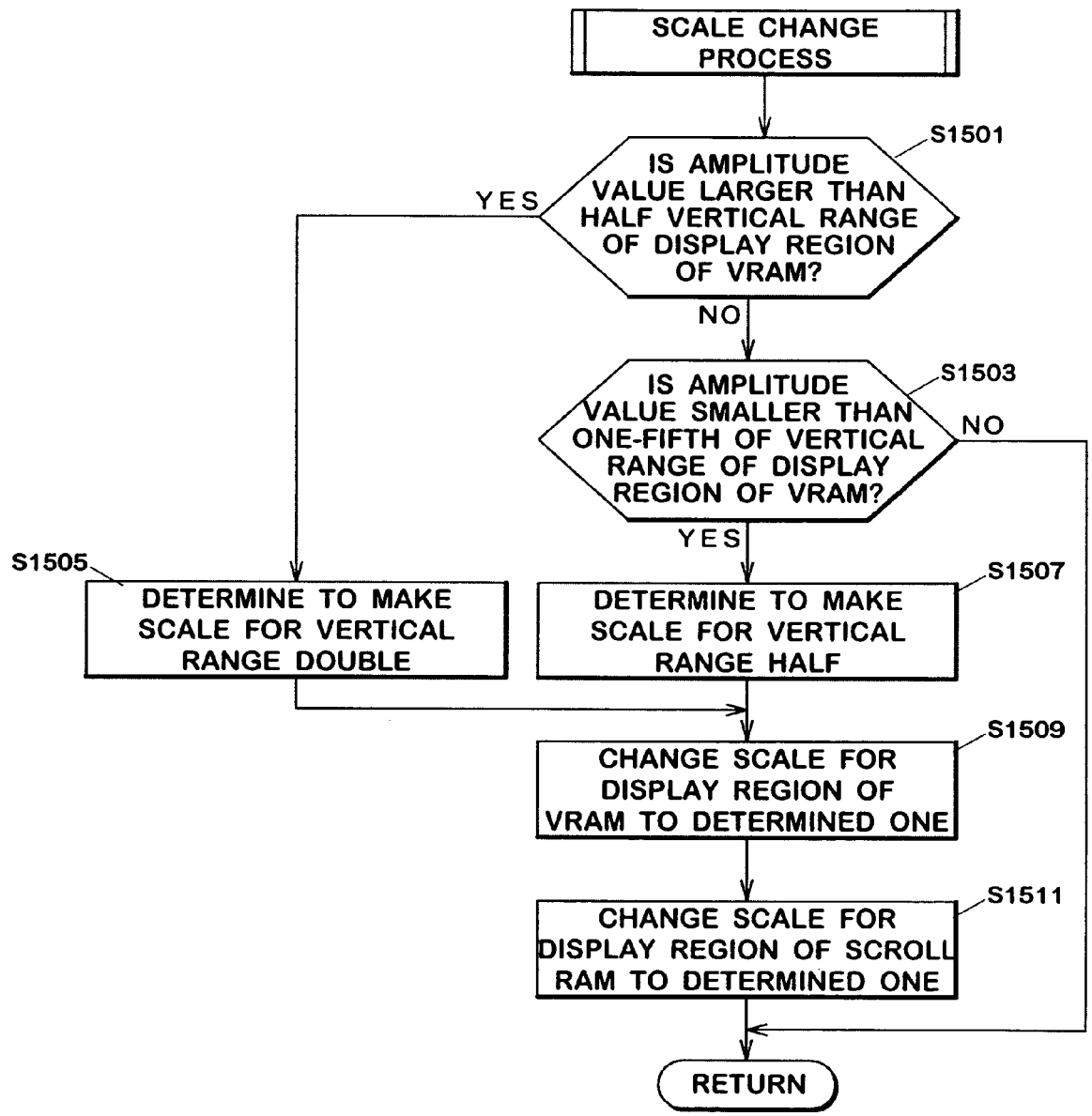
FIG. 15 is a flowchart of the scale change process according to the second embodiment.

With reference to flowcharts of FIG. 13-FIG. 15 and the like, details of a program for the scale change process performed by the CPU 10 of the electrocardiogram display device 100 are described. Various conditions in the second embodiment, such as the sampling frequency of electrocardiogram measurement data, the settings for the display regions of the VRAM 22 and the scroll RAM 24, the process for recognizing a heartbeat, and the drawing process, are similar the those in the first embodiment.

The CPU 10 sets a display region of the VRAM 22, where screen contents to be presented on the display 14 are recorded (step S1301 of FIG. 13), in the same manner as in the first embodiment. The CPU 10 sets the vertical range of a recording region of the scroll RAM 24 to three times that of the display region of the VRAM 22 (step S1303).

The CPU 10 measures a 12-lead electrocardiogram via the ECG electrodes 20 attached to the patient's body and the amplifier 11, to record electrocardiogram measurement data in the memory 16 (step S1305) (data acquisition means). Based on the acquired electrocardiogram measurement data, the CPU 10 records (draws) screen contents (electrocardiogram) for presentation on the display 14 in the VRAM 22 and the scroll RAM 24 (step S1307) (graph output means).

The CPU 10 determines whether or not a waveform corresponding to one heartbeat has been recognized (extracted) (step S1309). The determination in step S1309 is made in the same manner as in the first embodiment (refer to step S813 of FIG. 8). If it is determined in step S1309 that a waveform corresponding to one heartbeat has not been recognized, the CPU 10 repeats the processes in and after step S1305.

On the other hand, if it is determined in step S1309 that a waveform corresponding to one heartbeat has been recognized, the CPU 10 performs an amplitude value calculation process (step S1311). The amplitude value calculation process will be described later. In step S1309, in case of cardiac arrest (death), a P-wave and the like are not recognized. Therefore, in the embodiment, after electrocardiogram measurement data (normally, data to be displayed as a flat electrocardiogram) is acquired for one second, the CPU 10 performs the process of step S1311.

The CPU 10 determines whether or not amplitude values for the most recent twenty beats have been acquired (step S1313). If it is determined that the amplitude values for the most recent twenty beats have not been acquired, the CPU 10 repeats the processes in and after step S1305. On the other hand, if it is determined that the amplitude values for the most recent twenty beats have been acquired, the CPU 10 calculates an average of the amplitude values for the most recent twenty beats (which corresponds to "a value relating to an average of the amplitude data in a plurality of the cycles") (step S1315), and performs a scale change process (step S1317). Details of the scale change process will be described later.

After the process of step S1317, the CPU 10 determines whether or not the measurement is terminated (step S1319). If the measurement is not terminated, the CPU 10 repeats the processes in and after step S1305. On the other hand, if the measurement is terminated, the CPU 10 terminates the process.

6-3. Amplitude Value Calculation Process

Now, based on FIG. 14, a description is made of details of a program for the amplitude value calculation process performed in step S1311 of FIG. 13 as a subroutine.

The CPU 10 of the electrocardiogram display device 100 determines, based on the shape of the electrocardiographic waveform corresponding to one heartbeat recognized in step S1309 of FIG. 13, whether or not ventricular fibrillation is present (step S1401 of FIG. 14). If it is determined that ventricular fibrillation is not present, the CPU 10 determines whether or not cardiac arrest is present (step S1403). If cardiac arrest is present, the CPU 10 performs the process of step S1319 of FIG. 13. The determination in step S1401 and step S1403 is made in the same manner as in the first embodiment (refer to step S1001 and step S1003 of FIG. 10).

If it is determined in step S1403 that cardiac arrest is not present, the CPU 10 acquires data on an R potential and an S potential of the heartbeat recognized in step S1309 (step S1409), and calculates an amplitude value (step S1411). The amplitude value is calculated based on an "arithmetic expression: |R potential−S potential|" (absolute value of the difference between an R potential and an S potential). This amplitude value corresponds to the RS difference 40 in FIG. 4, or an amplitude value of a normal electrocardiographic waveform.

On the other hand, if it is determined in step S1401 that ventricular fibrillation is present, the CPU 10 acquires a maximum value (a local maximum in the object cycle) and a minimum value (a local minimum in the object cycle) of the recognized heartbeat (ventricular fibrillation waveform) (step S1405). The CPU 10 calculates an amplitude value of the ventricular fibrillation waveform (step S1407). The amplitude value is calculated based on an "arithmetic expression: (maximum value−minimum value)." This amplitude value corresponds to the difference 50 in FIG. 5.

Through the above processes, the CPU 10 calculates an amplitude value (amplitude data in the cycles) respectively for a normal case and a case of ventricular fibrillation, and then performs the processes in and after step S1313 of FIG. 13.

Data on amplitude values can be calculated using electric potential (voltage) values for a recognition point such as an R-wave of an electrocardiogram, position values (address values) in the scroll memory 24 corresponding to the position of the recognition point, or measured values in the display region corresponding to the position of the recognition point. In this embodiment, for illustration, electric potential (voltage) values are used in the calculation.

6-4. Scale Change Process

Now, based on FIG. 15, a description is made of details of a program for the scale change process performed in step S1317 of FIG. 13 as a subroutine.

The CPU 10 determines whether or not the average of the amplitude values calculated in step S1315 is larger than half of the vertical range of the display region of the VRAM 22 (step S1501). Specifically, since the width of the display region of the VRAM 22 is set from −1 mV to 1 mV in this embodiment (refer to step S1301 of FIG. 13), the CPU 10 determines whether or not the average of the amplitude values is larger than 1 mV.

If it is determined that the average of the amplitude values is not larger than half of the vertical range of the display region of the VRAM 22, the CPU 10 determines whether or not the average is smaller than one-fifth of the vertical range of the display region of the VRAM 22 (step S1503). Specifically, the CPU 10 determines whether or not the average of the amplitude values is smaller than 0.4 mV. If it is determined that the average of the amplitude values is not smaller than one-fifth of the vertical range of the display region of the VRAM 22, the CPU 10 performs the process of step S1319 of FIG. 13.

If it is determined in step S1501 that the average of the amplitude values is larger than half of the vertical range of the display region of the VRAM 22 (i.e., does not fit amplitude criteria or exceeds an upper amplitude criterion), the CPU 10 determines to make the vertical scale for the display region of the VRAM 22 "double" (step S1505). On the other hand, if it is determined in step S1503 that the average of the amplitude values is smaller than one-fifth of the vertical range of the display region of the VRAM 22 (i.e., does not fit amplitude criteria or falls short of a lower amplitude criterion), the CPU 10 determines to make the vertical scale for the display region of the VRAM 22 "half" (step S1507).

After the process of step S1505 or step S1507, the CPU 10 changes the scale for the display region of the VRAM 22 as determined (step S1509).

In cases of "double" in the scale change process, the data is replaced by data corresponding to a display region of a width from −2 mV to 2 mV (see FIG. 12A), as described in the above section of "6-1. Details of Scale Change Process." On the other hand, in cases of "half," the data is replaced by data corresponding to a display region of a width from −0.5 mV to 0.5 mV (see FIG. 12B).

After the process of step S1509, the CPU 10 changes the scale for the display region of the scroll RAM 24 as determined (step S1511). Because of this process, the CPU 10 can perform the drawing process and the scroll process of the first embodiment, even after the scale change process is performed, according to the recorded contents after the change process.

Through the above processes, the CPU 10 compresses or expands an electrocardiogram, and subsequently performs the process of step S1319.

The scale change process according to the second embodiment has been described above. It should be noted that the descriptions of the program, algorithms or the like of the process are made for illustration purposes. Thus, changes can be made by means known to those skilled in the art, of the timing to perform a scale change process, the settings of the size of the display regions of the VRAM and the scroll RAM (refer to steps S1301 and S1303 of FIG. 13, etc.), the criteria for determining the necessity for a scale change process (refer to steps S1501 and S1503 of FIG. 15), the settings for a scale change (refer to steps S1505 and S1507 of FIG. 15), and the like.

For example, a value calculated as "R value-S value" is used as an amplitude value for illustration (refer to step S1411 of FIG. 14), but another value calculated differently may be adopted. Instead of an average of amplitude data on twenty heartbeats, an average value of amplitude data on another number of heartbeats may be adopted, or amplitude data on one heartbeat may be based upon, to perform a scale change process.

The process of recognizing a waveform corresponding to one heartbeat in the first and second embodiments (refer to step S813 of FIG. 8 and step S1309 of FIG. 13) is based on whether or not data on respective recognition points between a P-wave and a P-wave of a next cardiac cycle has been extracted. The determination of the presence or absence of ventricular fibrillation of step S1001 of FIG. 10 and step S1401 of FIG. 14, and the determination of the presence or absence of ventricular arrest of step S1003 of FIG. 10 and step S1403 of FIG. 14, are made based on the presence or absence of a recognition point (representing a characteristic) in the electrocardiographic waveform, or based on the magnitude of amplitude of the waveform. Instead of utilizing data on all the recognition points such as P-wave, Q-wave, R-wave, S-wave and T-wave, the process of recognizing a waveform, determination of the presence or absence of ventricular fibrillation, and determination of the presence or absence of asystole may be performed, for example, by making a determination using data on part of the recognition points (for example, R-wave and S-wave), or using data representing another local maximum point or local minimum point. Recognition points (P-wave, Q-wave, R-wave, S-wave and T-wave) are not necessarily a local maximum point or a local minimum point, but may be any point defined by predetermined determination criteria.

The process of recognizing a waveform, determination of the presence or absence of ventricular fibrillation, and determination of the presence or absence of asystole may be performed, for example, utilizing an evaluation program as follows. However, note that the present invention is not limited to the use of them.

(List of Evaluation Programs)

(Program name/Principal Developer/Country)
    AVA/Pipberger/USA
    IBM/Bonner, Poppl/USA
    HP/Monroe/USA
    Marquette/Rowlandson/USA
    Nagoya/Okajima, Ohsawa/Japan 6-5. Presentation on Display in Second Embodiment (Scale Change Process)

Figure 16A:
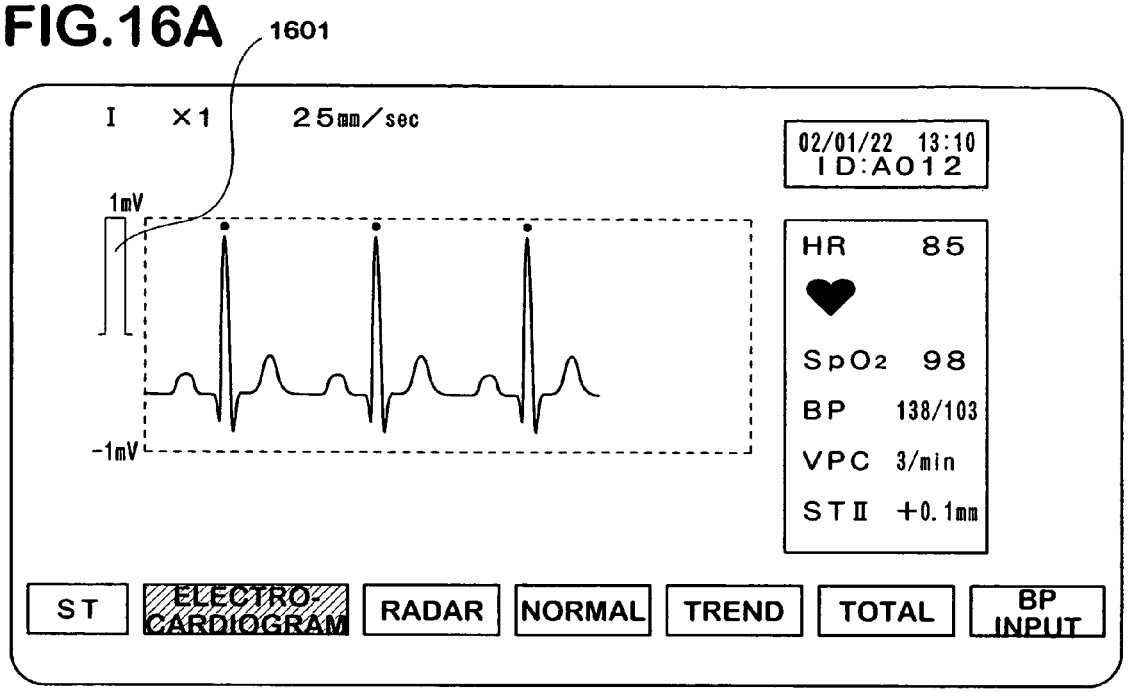
FIG. 16A and FIG. 16B show examples of a presentation on the display of the electrocardiogram display device during the scale change process.

FIG. 16 shows examples of a presentation on the display 14 in the second embodiment. FIG. 16A shows an example of a presentation on the display 14 before the scale change process. An electrocardiogram is displayed on the display 14. An electrocardiographic waveform criterion 1601, shown on the left side of the electrocardiogram, represents a criterion for a vertical width corresponding to a voltage of 1 mV.

Figure 16B:
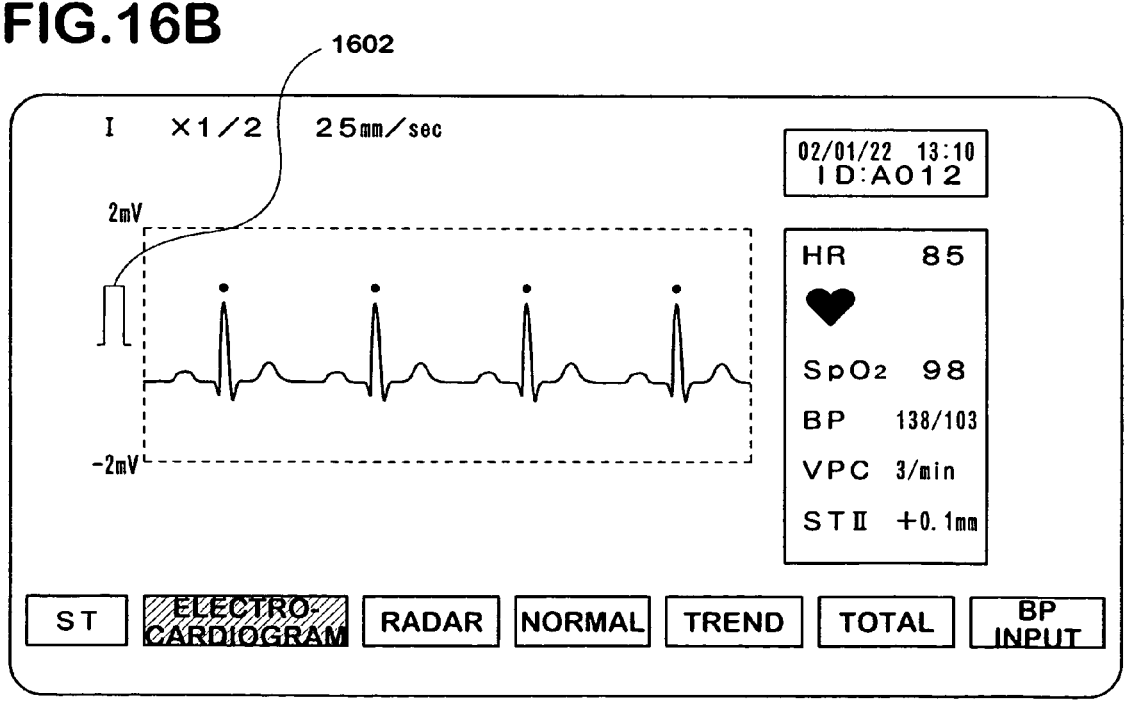

FIG. 16B shows an example of a presentation on the display 14 after the scale change process. An example where the scale is changed to "double" is shown (refer to step S1505 of FIG. 15). As a result of the scale change process, the electrocardiogram is displayed as compressed to half in the vertical direction. In this embodiment, in correlation with the scale change process, an electrocardiogram waveform criterion 1602 is also subjected to a scale change process. Specifically, the length of the electrocardiographic waveform criterion 1602 is changed to half that of the electrocardiographic waveform criterion 1601 of FIG. 16A. In cases where the scale is changed to "half," the electrocardiogram is displayed as expanded to double in the vertical direction and the length of the electrocardiographic waveform criterion is changed to double that of the electrocardiographic waveform criterion 1601.

The correspondence between a voltage value in the display 14 and a measured value on the display 14 is defined as 1 mV=1 cm in FIG. 16A, but in FIG. 16B, where the scale is changed to "double," as 1 mV=0.5 cm. In cases where the scale is changed to "half," it is defined as 1 mV=2 cm.

7. Effects of Embodiments 7-1. Effects of First Embodiment (Scroll Process)

According to the first embodiment, with each recognition of an electrocardiographic waveform corresponding to one heartbeat, the CPU 10 of the electrocardiogram display device 100 determines whether or not the heartbeat is displayed on the display 14 in such a manner as to facilitate viewing of the waveform shape for a user, and if it is not, the CPU 10 performs a scroll process on the electrocardiogram such that the heartbeat is displayed in a position that facilitates viewing of the waveform shape. Thus, the user of the electrocardiogram display device 100 can securely view the shape of an electrocardiographic waveform as a display object, and can therefore make an effective supplemental diagnosis (preliminary diagnosis) of a heart disease.

Here, a case where a heartbeat is not displayed in a position that allows a user to grasp the waveform shape generally refers to a case where an acquired cardiac electric potential includes noise. Specifically, when the intervals between the ECG electrodes 20 and the patient's heart vary, a swell occurs in low-frequency components. When such information including noise is AD converted and displayed as electrocardiogram measurement data, the position of the electrocardiogram on the display 14 may vary due to the presence of the noise. One cause of such a swell in noise-frequency components is a change due to the body movement of a patient during the measurement for an electrocardiogram. For example, in an ambulance, the body of a patient is not stable and therefore vertical fluctuations in the display position of an electrocardiogram may tend to occur occasionally.

In general conventional devices for displaying an electrocardiogram, a low-cut analogue filter is used to cut off low-frequency components which will generate noise, before information for an electrocardiogram is AD converted. In this manner, vertical fluctuations in the display position of an electrocardiogram are prevented. However, it is pointed out that the use of a low-cut analogue filter may cut off frequency components for a T-wave or an S-wave and may deform an electrocardiographic waveform (reference literature: Okajima and Hashiguchi, "Reliability of Electrocardiographic System," Industrial Publishing & Consulting, Inc., pp. 312-313).

In this embodiment, with this respect, vertical fluctuations of an electrocardiogram are corrected through digital processing, without the use of an analogue filter for low-frequency components which will generate noise. Therefore, the conventional problem of a deformed electrocardiographic waveform is resolved without cutting off frequency components necessary for display of an electrocardiographic waveform. Noise in high-frequency components such as hum, which may affect display of an electrocardiogram, may be cut off by a conventional method.

7-2. Effects of Second Embodiment (Scroll Process)

According to the second embodiment, with each recognition of a plurality of heartbeats, the CPU 10 of the electrocardiogram display device 100 determines whether or not the heartbeats are displayed in a size that facilitates viewing of the shape of the electrocardiographic waveform (including amplitude between an R-wave and an S-wave) for a user, and if they are not, the CPU 10 performs a scale change process on the electrocardiogram such that the electrocardiogram is displayed in a size that facilitates viewing of the waveform shape. Thus, the user of the electrocardiogram display device 100 can view the shape of an electrocardiographic waveform of an appropriate size, and can therefore make an effective supplemental diagnosis of a heart disease. Cases where the amplitude of an electrocardiographic waveform fluctuates may include, for example, a situation where the patient has an arrhythmia or is a neonatal baby, whose amplitude is smaller than normal.

According to the second embodiment, as indicated by the electrocardiographic waveform criterion 1601 of FIG. 16A and the electrocardiographic waveform criterion 1602 of FIG. 16B, the width (range) of the difference in electric potential as a criterion is correlated with the electrocardiogram. Thus, even when a scale change process has been performed, a user can easily identify the (electric potential difference) range of amplitude of electrocardiographic waveforms based on respective electrocardiographic waveform criteria.

8. Other Functions of Electrocardiogram Display Device

Now, a description is made of functions of the electrocardiogram display device 100 other than the foregoing scroll process and scale change process.

8-1. Indication of Heartbeat State

The electrocardiogram display device 100 indicates the state of heartbeats by the flashing of a predetermined symbol (mark) ("heartbeat information indication means for indicating information relating to heartbeats by changes in display mode"). Specifically, as shown in FIG. 11, the CPU 10 makes a heart mark flash on and off according to the beating of a heart under measurement.

This allows a user to confirm that the electrocardiogram display device 100 is in normal operation, as well as to grasp the state of heartbeats of a patient. In addition to, or as an alternative to, the flashing of a mark, a sound (for example, a pitch sound) may be outputted from the speaker 15 according to the beating of a heart.

8-2. Warning of Unanalyzable Conditions

During the process of displaying an electrocardiogram, the electrocardiogram display device 100 displays a predetermined warning in cases where the ECG electrodes 20 attached to the patient's body or the like have come off therefrom or in cases where a trouble has occurred in the process of preparing an electrocardiogram ("warning signal output means for outputting a warning signal in cases where display is inoperable"). Specifically, the CPU 10 displays a warning message such as "Electrodes detached" on the display 14.

This allows a user to immediately confirm that the process of preparing an electrocardiogram is interrupted by an accident. As an alternative to a warning message, the CPU 10 may change the color of display in total or in part, or may output a warning sound (such as alarm sound), to draw the attention of the user.

8-3. Indication of Recognition Points

The CPU 10 of the electrocardiogram display device 100 plots a recognition point 1105 as shown in FIG. 11. The recognition point 1105 mark is plotted at the position of an R-wave of each heartbeat. Specifically, the CPU 10 plots a recognition point with each recognition of a waveform corresponding to one heartbeat (refer to step S813 of FIG. 8). This allows a user of the electrocardiogram display device 100 to conveniently view the waveform shape of each cardiac cycle.

As a technique to plot (draw) a recognition point, means known to those skilled in the art may be adopted. This embodiment utilizes a recognition point plane (layer) where a recognition point is plotted, in addition to a plane where an electrocardiogram is displayed, as contents recorded in the VRAM 22. Specifically, with each recognition of the position of an R-wave, the CPU 10 plots a recognition point near the R-wave in the recognition point plane. At this time, regarding the plotted position of the recognition point, a calculation is performed only on the position in the time axis (X-axis)

direction, while the position in the electric potential axis (Y-axis) direction is fixed at a predetermined position in the vertical direction of the display region of the VRAM 22. When the electrocardiogram is displayed up to the right end of the display area, the recognition points are erased together with the electrocardiogram, and when a next electrocardiogram is drawn from the left end of the display area, a recognition point is drawn near an R-wave.

In this manner, by fixing the plotted position of recognition points in the vertical direction of the display area, the recognition points can be easily identified, even when the vertical positions of R-waves for respective waveforms fluctuate.

Indication of a recognition point is not limited to the recognition point 1105, but may be a vertical line displayed at the position of a P-wave on the display 14, a horizontal line showing the range from a P-wave to an S-wave, or a symbol such as "P" displayed at the position of a P-wave.

9. Other Embodiments, etc.

9-1. Variation Example of VRAM 22 and Scroll RAM 24 Configurations

In the first embodiment, the memory 16 is provided with a VRAM 22 that contents to be presented on the display 14 are recorded, and a scroll RAM 24 used by the CPU 10 to perform a scroll process; however, the present invention is not limited thereto. In another embodiment, the CPU 10 may be configured to perform a scroll process utilizing the recorded contents of the VRAM 22, without the use of a scroll RAM 24.

In the second embodiment, a scale change process is performed on both the VRAM 22 and the scroll RAM 24 (refer to steps S1509 and S1511 of FIG. 15); however, the present invention is not limited thereto. In another embodiment, the CPU 10 may perform a scale change process only on the scroll RAM 24 and copy the recorded contents of the scroll RAM 24 to the VRAM 22, in order to present an electrocardiogram after the scale change process on a display.

The processes of writing, erasing and rewriting of the recorded contents of the VRAM 22 and the scroll RAM 24 may be changed by means known to those skilled in the art. For example, the process of copying (rewriting) the recorded contents of the scroll RAM 24 to the VRAM 22 may be performed by rewriting only a portion on which a scroll process or a scale change process has been performed, instead of rewriting the entire recorded contents of the VRAM 22.

9-2. Variation Example of Scroll Process

Figure 17A:
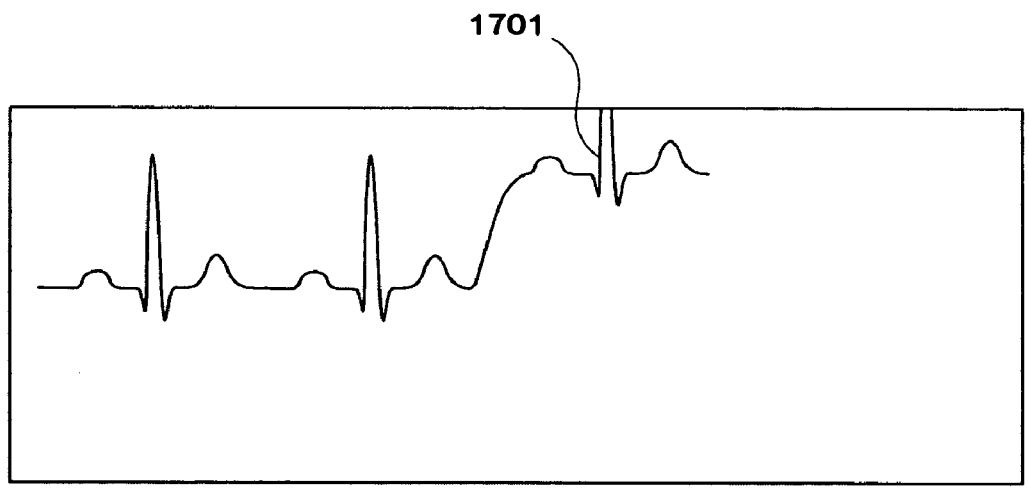
FIG. 17A and FIG. 17B show another embodiment of the scroll process.
Figure 17B:
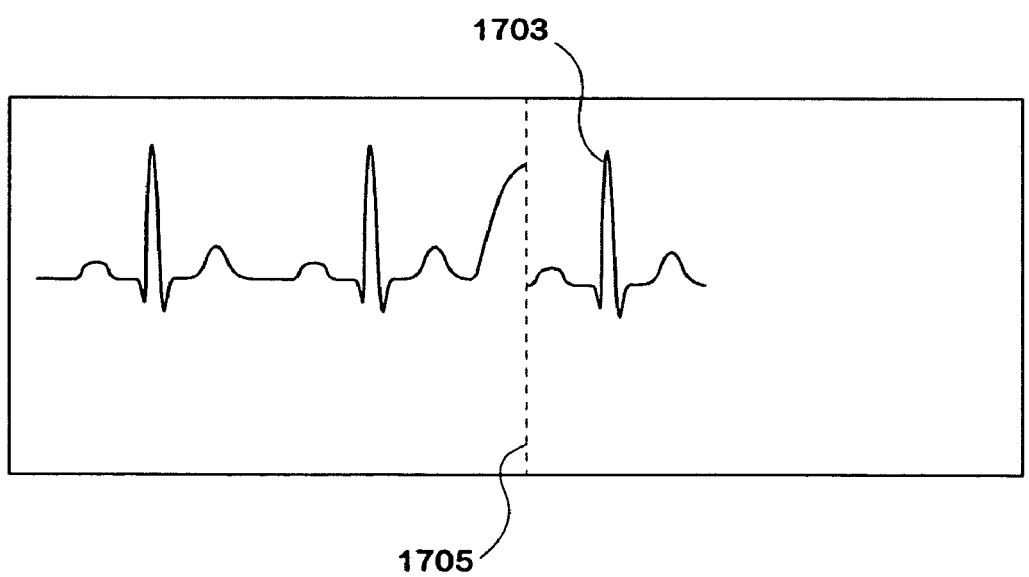

In the first embodiment, a scroll process is performed on an entire electrocardiogram, including heartbeats in the past, so that the shape of a recognized electrocardiographic waveform is presented in an appropriate position on a display (refer to steps S903 and S905 of FIG. 9, or the like); however, the present invention is not limited thereto, but a scroll process may be performed only on the most recent portion of the electrocardiogram recognized. Specifically, the CPU 10 performs a scroll process on an electrocardiographic waveform corresponding to a recognized heartbeat on the scroll RAM 24 and then selectively cuts out a portion (from a P-wave to a next P-wave) of the electrocardiographic waveform corresponding to the recognized heartbeat, to copy only the portion of the electrocardiographic waveform to the VRAM 22. FIG. 17 illustrates such a scroll process. As shown in FIG. 17A, an R-wave of the most recent electrocardiographic waveform of an electrocardiogram 1701 is not displayed. Then, as shown in FIG. 17B, a portion of the electrocardiographic waveform on the right side of a P-wave position 1705 is cut out and subjected to a scroll process, to form an electrocardiogram 1703. In this case, the CPU 10 may affix positional information to data as the data is recorded in the VRAM 22 or the scroll RAM 24, such that the data can be cut out by the cycle (allow the data to be recorded so as to be dividable for each object cycle).

The first embodiment uses an algorithm for moving a central point of an electrocardiographic waveform corresponding to a recognized heartbeat to the position of a median for the scroll RAM 24, to perform a scroll process; however, the present invention is not limited thereto. In another embodiment, only the position of a cut-out portion of the scroll RAM 24 (a display region portion) may be changed, instead of moving an electrocardiogram itself.

Figure 19:
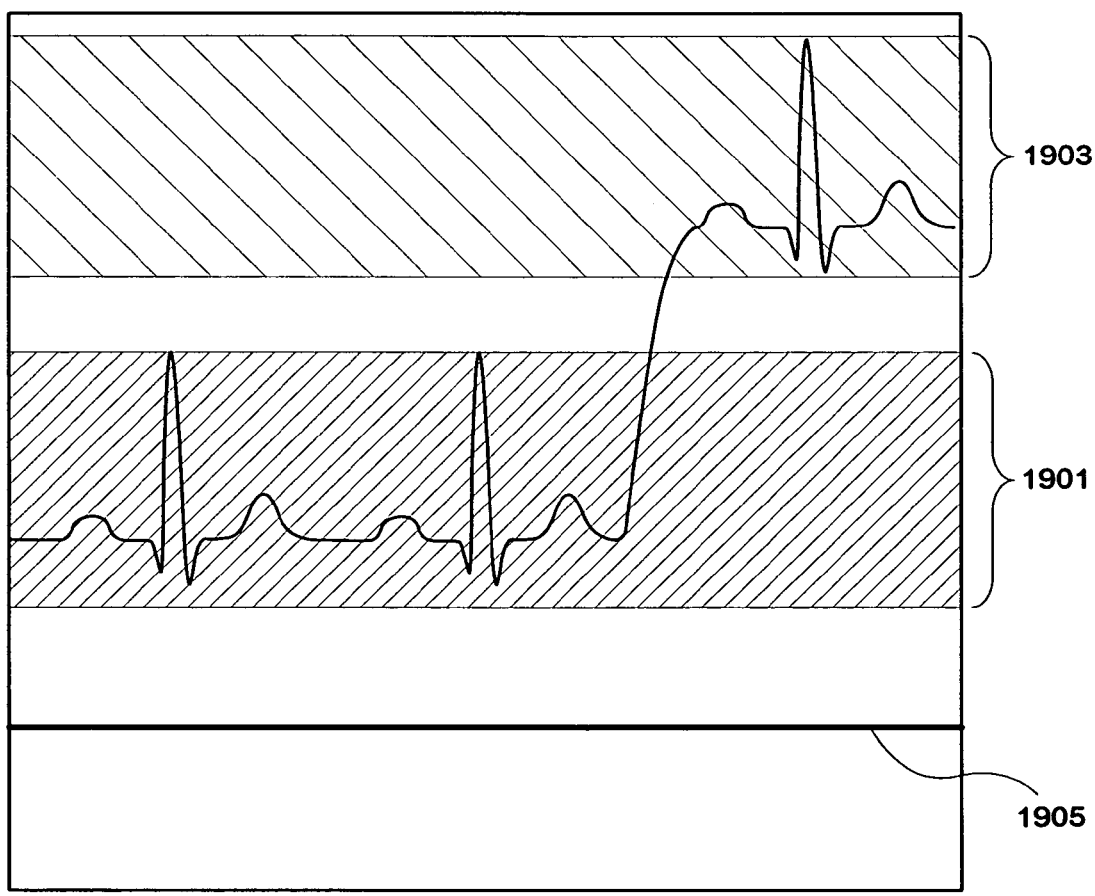
FIG. 19 shows another embodiment of the scroll process.

FIG. 19 schematically shows recorded contents of the scroll RAM 24 for performing such a scroll process. Specifically, in FIG. 19, a display region portion 1901 of the scroll RAM 24 is normally correlated with the display region of the VRAM 22. A change is made to the display region portion of the scroll RAM 24 (a portion copied to the VRAM 22), such that a display region portion 1903 is correlated with the display region of the VRAM 22 after a scroll process is terminated. However, the change of the display region portion may be completed in a predetermined loop count, to achieve a smooth scroll process. The display region portions 1901 and 1903 can be defined by a median, vertical width values, or the like. In cases of such a scroll process, when the measurement data is drawn beyond an upper portion of the display region of the scroll RAM 24, such measurement data may be drawn below a reference line 1905. Specifically, the reference value line 1905 is set as a lower limit of the measurement data that can be recorded in the scroll RAM 24, and the lower side of the reference line 1905 is set as an upper limit of the scroll RAM 24. This allows part of the data beyond the upper portion of the scroll RAM 24 to be drawn below the reference line 1905. When the recorded contents of the scroll RAM are copied to the VRAM 22, the data drawn in the upper portion of the scroll RAM 24 and the data drawn below the reference line 1905 may be combined and then copied. The reference line 1905 position may be set at the lower end of the scroll RAM 24 at the start of electrocardiogram measurement, and may be changed to a position where the upper and lower display widths (electric potential value widths) that allow drawing are equal with respect to the display region portion, depending on the fluctuations of the display region portion. This allows the display region of the scroll RAM 24 to always keep equal upper and lower display regions using the most recent electrocardiogram measurement data as a reference.

Figure 18A:
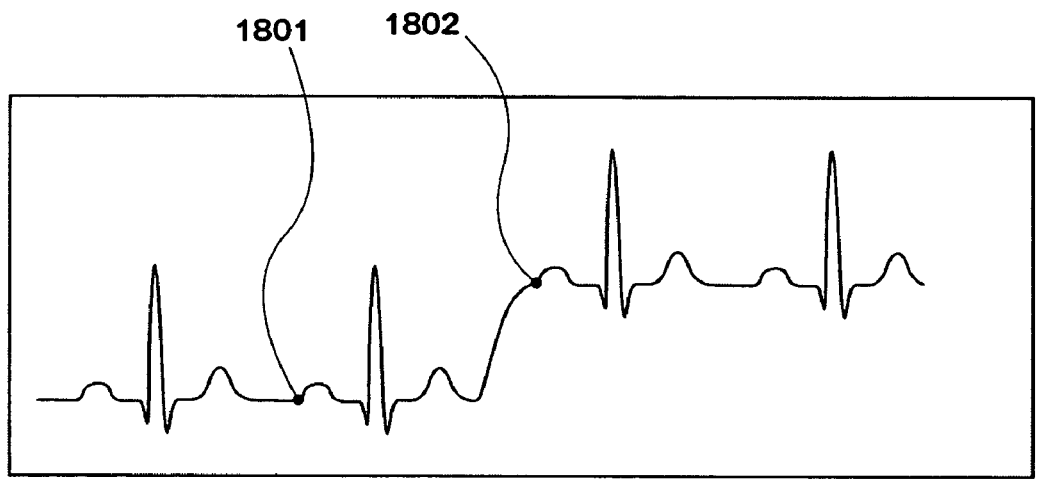
FIG. 18A and FIG. 18B show another embodiment of the scroll process.
Figure 18B:
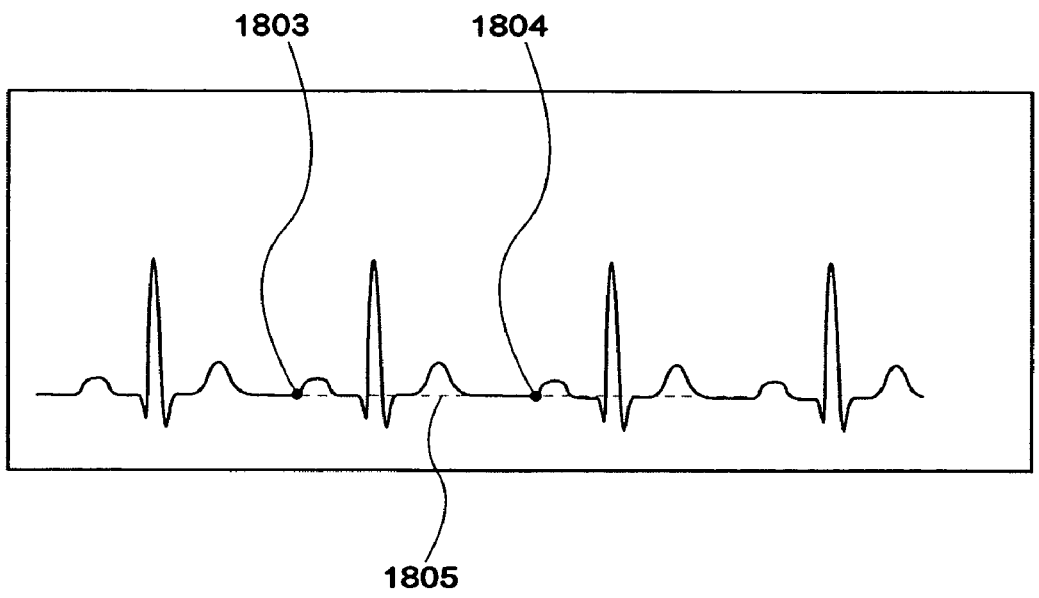

In the scroll process (shift process) in the first embodiment, an entire electrocardiogram is translated in the vertical direction so that an electrocardiographic waveform corresponding to a recognized waveform is appropriately presented on a display; however, the present invention is not limited thereto. In another embodiment, an image correction process may be performed on an electrocardiographic waveform corresponding to each heartbeat, instead of translating an entire electrocardiogram, so that the waveform is appropriately presented on a display. Specifically, a linear interpolation (or a spline interpolation) is performed on an electrocardiographic waveform corresponding to each heartbeat being displayed, using a P-wave position of the heartbeat as a reference, so as to make a presentation in which P-wave positions are uniform (flat) in the vertical direction on a display (baseline correction means for correcting display such that the baseline of an electrocardiographic waveform (lines connecting a P-wave of a certain heartbeat and a P-wave of a next heartbeat) is uniform). FIG. 18 illustrates such a scroll process (image correction process). In an electrocardiogram of FIG. 18A, a P-wave position 1801 and a P-wave position 1802 are not uniform in height. When such a scroll process is performed, a P-wave position 1803 and a P-wave position 1804 are made uniform on a baseline 1805, as shown in FIG. 18B. The baseline 1805 is a line extending in parallel with the horizontal axis of a display, and may or may not be presented on the display.

In the first embodiment, the vertical range of the display region of the scroll RAM 24 is set to three times that of the display region of the VRAM 22 (refer to step S803 of FIG. 8); however, the present invention is not limited thereto. The display region of the scroll RAM 24 may be set such that the electrocardiogram will not go out of the display region in consideration of the condition of electrocardiogram measurement on a patient.

However, in cases where an electrocardiographic waveform goes out of the display region of the scroll RAM 24, or in other words, in cases where acquired voltage values for electrocardiogram measurement data deviate from the voltage value range of the display region of the scroll RAM 24, the voltage value range of the display region of the scroll RAM 24 may be reset to draw the electrocardiographic waveform, for example. Alternatively, the recorded contents of the VRAM 22 may be presented on a display as they are (with the electrocardiographic waveform undisplayed), as an undisplayable state, without performing a scroll process. Also, in cases where an electrocardiographic waveform corresponding to a recognized heartbeat goes out of the display region of the scroll RAM 24, the recorded contents of the scroll RAM 24 and the VRAM 22 may be erased, and then the voltage value range of the display region of the scroll RAM 24 and the VRAM 22 may (or may not) be reset, to start the process of writing an electrocardiogram from a heartbeat next to the recognized heartbeat, again from the left of the display region.

9-3. Variation Example of Setting of Central Point

In the first embodiment, a central point of an electrocardiographic waveform is calculated as a point dividing a segment between an R-wave height and an S-wave height at a ratio of 1:2 (refer to step S1011 of FIG. 10); however, the present invention is not limited thereto. Changes may be made to the position of a central point and the calculation method thereof, by means known to those skilled in the art. For example, an average of a plurality of central points of electrocardiographic waveforms may be adopted; a central point may be calculated with a P potential as a reference; a central point may be calculated using a Q potential instead of an S potential; or a central point may be calculated based on the graphical characteristics of a QRS shape (triangular shape).

9-4. Variation Example of Scale Change Process

In the scale change process in the second embodiment, a scale change (compression or expansion) is performed on an electrocardiogram to be displayed on the display 14, by changing the scale for the display region of the VRAM 22 to a predetermined one; however, the present invention is not limited thereto. In another embodiment, the process of changing the scale may be performed as the recorded contents of the VRAM 22 are read, without changing the scale for the display region of the VRAM 22 (without rewriting the memory contents).

In the second embodiment, a process is performed that changes the scale for the display region of the VRAM 22 and that for the display region of the scroll RAM 24 to a predetermined one (refer to steps S1509 and S1511 of FIG. 15); however, the present invention is not limited thereto. In another embodiment, the recorded contents of the memories may be erased, and then the scale for the display region of the VRAM 22 and that for the display region of the scroll RAM 24 may be reset (compressed or expanded), to start the process of writing an electrocardiogram as the scale is changed, again from the left side of the display region, instead of performing a scale change process on the display region of the VRAM 22 and the display region of the scroll RAM 24, or in other words, performing the process of rewriting the recorded contents of the memories.

9-5. Variation Example of Electrocardiographic Display

In the embodiments, an electrocardiogram presented on the display 14 is taken as an example of the "graph output means". As other embodiments of the "graph output means," data for graph display may be outputted to a recording medium such as memory card and CD-ROM, outputted over communication means (such as LAN, Ethernet (registered trademark), telephone circuit, wireless communication, Internet, wire, infrared communication, cellular, Bluetooth and PHS), outputted for the purpose of file copy between two devices via a portable medium (for example, writing in a PCMCIA memory card, or the like), outputted as a hard copy by being printed out, outputted by a facsimile machine, or the like.

The term "graphical representation" used in the claims involves the general concept including a graph outputted so as to be visually recognized. For example, the concept includes an electrocardiogram presented on a display, drawn by a plotter, outputted as a hard copy, outputted by a facsimile machine, or the like (the output destination corresponds to the "output region").

In cases where a scroll process according to the first embodiment is performed when a graphical representation is outputted as a hard copy by being printed out, outputted by a facsimile machine or the like, an electrocardiogram where a scroll process is performed for each heartbeat is outputted to such a hard copy or a facsimile sheet. When such an output is required, only a recognized portion of an electrocardiographic waveform may be subjected to a scroll process and then outputted, for example, because of the presence of restrictions on the sheet width or the like. Specifically, the CPU 10 performs a scroll process on an electrocardiographic waveform corresponding to a recognized heartbeat on the scroll RAM 24 and then selectively cuts out a portion (from a P-wave to a next P-wave) of the electrocardiographic waveform corresponding to the recognized heartbeat, to copy only the portion of the electrocardiographic waveform to the VRAM 22. The output results will take a shape in which the portion of the electrocardiographic waveform where a scroll process has been performed is cut out (the graph line is discontinuous before and after a cut) (the position of the graph in the output region is corrected for each cycle of the data) (see FIG. 17B). However, a linear interpolation process or the like may be performed so that such a discontinuous shape will not appear in the output.

In the embodiments, a graphical representation is indicated by a continuous straight or curved line; however, the present invention is not limited thereto. It may be indicated by a discontinuous straight or curved line, or mere predetermined data points plotted.

9-6. Example of Data for Graph Display

In the embodiments, electrocardiogram measurement data is used as an example of data; however, the present invention is not limited thereto. In other embodiments, information with certain periodicity (which may include biological information) may be used as data in the present invention. Specifically, the present invention allows monitoring a machine, determining its failure status, and so on, based on the graphical representation of an electric current or voltage waveform as a periodic signal from the machine. The present invention can also adopt data representing optical waveforms, sound waveforms, seismic waveforms, and the like. The present invention is suitable for cases where observation of the waveform shape for each cycle is important in grasping the state of a data object.

The present invention is not limited to dealing with data with periodicity, but may be used to change the form of graph display of general data presented chronologically such that data for a certain time interval is displayed appropriately. Specifically, for example, it may be determined whether or not data for the most recent five seconds is displayed appropriately in the display area of the display 14 (determining whether or not data for a predetermined interval is displayed appropriately as a graph in the output region), and if it is not displayed appropriately, a scroll process or a scale change process may be performed on an entire graph or a part of the graph corresponding to the most recent five seconds such that the data for the most recent five seconds is displayed appropriately in the display area of the display 14. The "predetermined interval" includes an entire display area (an entire output region), or a part of a display area (a part of an output region).

9-7. Variation Example of Device Configuration

In the embodiments, the electrocardiogram display device 100 performs the measurement process for an electrocardiogram, the scroll process and the scale change process. However, another device configuration may be adopted in which these processes are performed by more than one separate device. The configuration of devices (the number and combination of devices) for performing the measurement process for an electrocardiogram, the scroll process and the scale change process, and the configuration of the CPU may be changed by means known to those skilled in the art.

For example, a configuration is possible in which a device for measurement for an electrocardiogram and extraction of recognition value data and a device for display of an electrocardiogram are provided as separate devices. Specifically, a first device installed in an ambulance performs measurement for an electrocardiogram and records electrocardiographic waveform data, and based on the electrocardiographic waveform data, extracts recognition value data. Then, a second device installed in a hospital receives the electrocardiographic waveform data and the recognition value data sent from the first device, and displays an electrocardiogram and performs a scroll process (first embodiment) or a scale change process (second embodiment) (the second device corresponds to the term "graph display control device" used in the claims). Communication means between the first device and the second device may be LAN, Ethernet (registered trademark), telephone circuit, wireless communication, Internet, wire, infrared communication, cellular, Bluetooth, PHS, or the like. Alternatively, file copy may be performed between the two devices via a portable medium (for example, transfer by a PCMCIA memory card, or the like).

Other auxiliary devices may be connected to the electrocardiogram display device 100. Specifically, a blood pressure meter may be connected to the electrocardiogram display device 100 as an auxiliary device to display "blood pressure (BP)," or a blood oxygen saturation level meter to display "blood oxygen saturation level ($SpO_2$)."

9-8. Application Example of Electrocardiogram Display Device

In the embodiments, a case where the electrocardiogram display device 100 is used in an ambulance is taken as an example; 66 wever, the present invention is not limited thereto, but the device may be adapted to be carried to an emergency medical site, installed in household for home medical use, or used extensively for living bodies including humans and animals. For example, in a case of a small electrocardiogram display device, a display can be made small by correlating its horizontal axis (time) measured value of 12.5 mm to one second.

A device with a function similar to that of the electrocardiogram display device 100 may be installed in an operator's seat of an automobile or a train, a cockpit of an airplane, or the like, to prevent a serious accident from happening due to an attack of myocardial infarction or the like, or installed in a toilet seat or the like for daily health care purposes. At this time, the ECG electrodes 20 or the like need to be installed where the body of an object person will inevitably touch, such as, for example, handle, toilet seat, or handrail.

9-9. Example of Program Execution Method, etc.

In the embodiments, a program for operation of the CPU 10 is stored in the F-ROM 17; however, the program may be stored in and read from a CD-ROM and installed to a hard disk or the like. The program may be stored in and installed from a recording medium readable by a computer other than a CD-ROM, such as a DVD-ROM, a flexible disk (FD) or an IC card. The program may be downloaded through a communication line. The program stored in a CD-ROM may be executed directly by a computer, instead of being installed from a CD-ROM and executed indirectly by a computer.

Programs executable by a computer include those which become executable when simply installed, those requiring conversion to a different form (for example, decompression of compressed data), and those which become when combined with another module.

In the above embodiments, the functions shown in FIG. 1 are implemented by a CPU and a program; however, part or all of the functions may be constructed by a hardware logic (logic circuit).

The outline and preferred embodiments of the present invention have been described above. The terms used herein are intended not for limitation purposes, but for illustration purposes. Those skilled in the art to which the present invention relates may modify and practice the system, device and method described in relation to the present invention. Thus, such modifications are considered to fall within the scope of the present invention.

What is claimed is:

1. An electrocardiogram display method for displaying an electrocardiogram in an output region based on electrocardiogram measurement data, comprising:

receiving electrocardiogram measurement data including noise which affects a display position of an electrocardiogram;

displaying an electrocardiogram in the output region based on the electrocardiogram measurement data;

determining a cardiac cycle of the electrocardiogram as a display object;

determining, based on data on the cardiac cycle, whether or not an electrocardiogram included in the cardiac cycle is displayed appropriately in the output region;

when it is determined that the electrocardiogram included in the cardiac cycle is not displayed appropriately in the output region due to a presence of the noise, scrolling the electrocardiogram for the cardiac cycle in the output region in a direction of cardiac electric potential variation components in order that the cardiac cycle to be displayed in the output region; and wherein in said scrolling, the electrocardiogram is shifted in a direction of cardiac electric potential variation components without causing a deformation of waveform.

2. An electrocardiogram display method for displaying an electrocardiogram while performing a display position correction process in order that a cardiac cycle of an electrocardiogram based on electrocardiogram measurement data to be displayed in an output region, comprising the steps of:

receiving electrocardiogram measurement data;

determining a cardiac cycle of an electrocardiogram based on the electrocardiogram measurement data;

performing a display position correction process such that an electrocardiogram included in the cardiac cycle is displayed appropriately in the output region, in correlation, in terms of timing, with the process of determining a cardiac cycle; and wherein when the electrocardiogram included in the cardiac cycle is not displayed appropriately, the electrocardiogram is shifted in a direction of cardiac electric potential variation components without causing a deformation of waveform.

3. An electrocardiogram display method for displaying an electrocardiogram in an output region of a display based on electrocardiogram measurement data, comprising:

receiving electrocardiogram measurement data, the electrocardiogram measurement data including noise which affects a displayed position of the electrocardiogram;

displaying an electrocardiogram representing the electrocardiogram measurement data in the output region;

determining a cardiac cycle of the electrocardiogram as a display object;

determining, based on data on the cardiac cycle, whether or not an electrocardiogram included in the cardiac cycle is displayed appropriately in the output region; and when it is determined that the electrocardiogram included in the cardiac cycle is not displayed appropriately in the output region, shifting the electrocardiogram displayed in the output region in a direction of cardiac electric potential, wherein the shifting is performed by changing respective coordinates of an upper limit, a lower limit and a median in a vertical direction by a predetermined number of units and then redrawing the electrocardiogram in the output region, wherein the electrocardiogram is shifted without causing a deformation of a waveform.

* * * * *